US011944639B2

(12) United States Patent
Wilmotte et al.

(10) Patent No.: US 11,944,639 B2
(45) Date of Patent: *Apr. 2, 2024

(54) PREVENTIVE AND CURATIVE PEROXOMETALLATE BASED COMPOSITION, NOTABLY PHARMACEUTICAL COMPOSITION

(71) Applicant: OXYMO TECHNOLOGIES INC., Québec (CA)

(72) Inventors: Rémi Wilmotte, Chalons-sur-Vesles (FR); Frédéric Lorenzo, Seine-Port (FR); Denis Olivier Chretien, La Garenne Colombes (FR)

(73) Assignee: OXYMO TECHNOLOGIES INC., Québec (CA)

( * ) Notice: Subject to any disclaimer, the term of this patent is extended or adjusted under 35 U.S.C. 154(b) by 369 days.

This patent is subject to a terminal disclaimer.

(21) Appl. No.: 17/073,026

(22) Filed: Oct. 16, 2020

(65) Prior Publication Data

US 2021/0030788 A1 Feb. 4, 2021

Related U.S. Application Data

(63) Continuation of application No. 16/089,757, filed as application No. PCT/IB2017/051797 on Mar. 29, 2017, now Pat. No. 10,857,179.

(30) Foreign Application Priority Data

Mar. 29, 2016 (FR) ..................................... 16 52697

(51) Int. Cl.
| | |
|---|---|
| *A61K 33/24* | (2019.01) |
| *A61K 9/00* | (2006.01) |
| *A61K 9/08* | (2006.01) |
| *A61K 33/242* | (2019.01) |
| *A61K 33/244* | (2019.01) |
| *A61K 33/40* | (2006.01) |
| *A61K 47/08* | (2006.01) |
| *A61K 47/18* | (2017.01) |
| *A61P 31/22* | (2006.01) |

(52) U.S. Cl.
CPC ............ *A61K 33/24* (2013.01); *A61K 9/0014* (2013.01); *A61K 9/0034* (2013.01); *A61K 9/0048* (2013.01); *A61K 9/006* (2013.01); *A61K 9/08* (2013.01); *A61K 33/242* (2019.01); *A61K 33/244* (2019.01); *A61K 33/40* (2013.01); *A61K 47/08* (2013.01); *A61K 47/183* (2013.01); *A61P 31/22* (2018.01)

(58) Field of Classification Search
CPC .......... A61P 31/00; A61P 31/02; A61P 31/04; A61K 9/0014; A61K 33/24; A61K 33/242; A61K 33/244; A61K 33/40

See application file for complete search history.

(56) References Cited

U.S. PATENT DOCUMENTS

| | | | |
|---|---|---|---|
| 10,857,179 B2 * | 12/2020 | Wilmotte | ................ A61P 31/22 |
| 2003/0039702 A1 | 2/2003 | Shigeta et al. | |
| 2007/0059255 A1 | 3/2007 | Tichy et al. | |
| 2011/0123642 A1 * | 5/2011 | Wilmotte | ............... A01N 59/00 |
| | | | 424/616 |
| 2014/0322333 A1 | 10/2014 | Stadler et al. | |

FOREIGN PATENT DOCUMENTS

| | | |
|---|---|---|
| CN | 105408257 A | 3/2016 |
| JP | 61-63619 A | 4/1986 |
| JP | 64-38022 A | 2/1989 |
| JP | H05-320059 A | 12/1993 |
| JP | 2000-229864 A | 8/2000 |
| WO | WO 2005/010774 | 2/2005 |
| WO | WO 2010/004161 | 1/2010 |

OTHER PUBLICATIONS

International Search Report, PCT/PCT/IB2017/051797, dated Jun. 30, 2017.
Balcerzak M. et al (2004) "Spectrophotometric studies of the interaction of noble metals with quercetin and quercetin-5'-sulfonic acid", Anal. Sci., 20(9), 1333-1337.
Balcerzak M. et al (2008) "Selective determination of Fe(III) in Fe(II) samples by UV-spectrophotometry with the aid of quercetin and morin", Acta Pharm., 58, 327-334.
Bielski B.H. et al (1985) "Reactivity of HO2/O2-radicals in aqueous solution", J. Phys. Chem. Ref. Data, 14(4), 1041-1100.
Böhme K. et al (1992) "Generation of singlet oxygen from hydrogen peroxide disproportionation catalyzed by molybdate ions", Inorg. Chem., 31, 3468-3471.
Britigan B.E. et al (1998) "Binding of iron and inhibition of iron-dependent oxidative cell injury by the "calcium chelator" 1,2-bis(2-aminophenoxy)ethane N, N, N', N'-tetraacetic acid (BAPTA)", Biochem. Pharmacol., 55(3), 287-295.
Contreras R. et al (2010) "Type of cell death induced by seven metals in cultured mouse osteoblastic cells", in vivo, 24, 507-512.
Dement'ev I.A. et al (2007)"Mononuclear, polynuclear, and cluster complexes of molybdenum and their reactions as models of biochemical systems and processes", Russ. J. Gen. Chem., 77(5), 822-843.

(Continued)

*Primary Examiner* — Michael B. Pallay
(74) *Attorney, Agent, or Firm* — NIXON & VANDERHYE

(57) ABSTRACT

The invention concerns a mixture or a composition, that is preferably therapeutically active by topical administration, comprising: —at least one metal salt, the metal being chosen from molybdenum (Mo), tungsten (V), vanadium (V), gold (Au), a lanthanide, in particular lanthanum; —at least one chelating agent; —at least one source of peroxidative radicals; —at least one buffer agent; and pharmaceutical compositions constituted by or comprising said mixture, the methods for producing same and applications thereof, in particular in a method for the therapeutic treatment of a viral infection, and in particular involving a virus of the Herpesviridae family; or as an anti-inflammatory.

31 Claims, 8 Drawing Sheets

(56) References Cited

OTHER PUBLICATIONS

Elnemma E. (2004) "Spectrophotometric determination of hydrogen peroxide by a hydroquinone-aniline system catalyzed by molybdate", Bull. Korean Chem. Soc., 25(1), 127-129.

Kim M.-J. et al "Adsorption of Molybdate onto Hematite: Kinetics and Equilibrium" in Water and geoscience: proceedings of the 5th IASME/WSEAS International Conference on Water Resources, Hydraulics & Hydrology (WHH 10), proceedings of the 4th IASME/WSEAS International Conference on Geology and Seismology (GES '10) : University of Cambridge, UK, Feb. 23-25, 2010, pp. 170-173.

Kolthoff I.M. et al (1951) "Catalytic Polarographic Waves of Hydrogen Peroxide. II. Kinetic Waves for the Peroxy Compounds of Molybdenum(VI), Tungsten(VI) and Vanadium(V)", J. Am. Chem. Soc., 73(11), 5315-5321.

Koppenol W.H. (1985) "The reaction of ferrous EDTA with hydrogen peroxide: evidence against hydroxyl radical formation", J. Free Radic. Biol. Med., 1(4), 281-285.

Koppenol W.H. (2001) "The Haber-Weiss cycle—70 years later", Redox Report, 6(4), 229-234.

Kwon B.G. et al (2006) "Determination of Hydroperoxyl/superoxide Anion Radical (HO2•/O2•-) Concentration in the Decomposition of Ozone Using a Kinetic Method", Bull. Korean Chem. Soc., 27(11), 1785-1790.

Lambers H. et al (2006) "Natural skin surface pH is on average below 5, which is beneficial for its resident flora", Int. J. Cosmet. Sci., 28(5), 359-370.

Lin H.-B. et al (2006) "Ethylenediamine Tetraacetato Trioxomolybdate(VI) and Tungstate(VI) and their Reactions with Hydrogen Peroxide" Synthesis and Reactivity in Inorganic, Metal-Organic, and Nano-Metal Chemistry, 36(5), 411-414.

Ma Z. et al (2013) "A Novel Protocol for Oxidative Degradation of Chitosan with Hydrogen Peroxide Catalyzed by Peroxomolybdate in aqueous Solution", RSC Adv., 3, 12049-12051.

Martins A.P. et al (2013) "Aquaporin Inhibition by Gold(III) Compounds: New Insights", Chem. Med. Chem., 8(7), 1086-1092.

Niemietz C.M. et al (2002) "New potent inhibitors of aquaporins: silver and gold compounds inhibit aquaporins of plant and human origin", FEBS Lett., 531(3), 443-447.

Noble R.W. et al (1970) "The reaction of ferrous horseradish peroxidase with hydrogen peroxide", J. Biol. Chem., 245(9), 2409-2413.

Oyerinde O.F. et al (2008) "Solution structure of molybdic acid from Raman spectroscopy and DFT analysis", Inorganica Chimica Acta, 361, 1000-1007.

Rahuma M.N. et al (2013) "Cleaner production in chemical and petrochemial industries", Int. J. Res. Environ. Sci. Technol., 3(1), 26-28.

Rush J.D. et al (1986) "Oxidizing intermediates in the reaction of ferrous EDTA with hydrogen peroxide. Reactions with organic molecules and ferrocytochrome c", J. Biol. Chem., 261(15), 6730-6733.

Rush J.D. et al (1990) "Distinction between hydroxyl radical and ferryl species", Methods Enzymol., 186, 148-156.

Tsien R.Y. (1980) "New calcium indicators and buffers with high selectivity against magnesium and protons: design, synthesis, and properties of prototype structures", Biochemistry, 19(11), 2396-2404.

Van Der Zee J. et al (1993) "Hydroxyl radical generation by a light-dependent Fenton reaction", Free Rad. Biol. Med., 14(2), 105-113.

Vyskocil A. et al (1999) "Assessment of molybdenum toxicity in humans", J. Appl. Toxicol., 19(3), 185-192.

Yamamoto A. et al (1998) "Cytotoxicity evaluation of 43 metal salts using murine fibroblasts and osteoblastic cells", J. Biomed. Mater. Res., 39(2), 331-340.

Zhou Z.H. et al (2004) "Peroxomolybdate(VI)-citrate and- malate complex interconversions by pH-dependence. Synthetic, structural and spectroscopic studies", Dalton Trans., 9, 1393-1399.

French Search Report, FR 1652697, dated Sep. 22, 2016.

Yu. L. Suponitskiy et al., Thermodynamic Properties of Lanthanum Molybdates, Russian Journal of Physical Chemistry A, Feb. 2016, vol. 90, Issue 2, pp. 267-270.

Office Action issued in Japanese Patent Application No. 2018-551991 dated May 31, 2022.

"Metal salt," You-iggy [online], May 20, 2022 (searched on May 25, 2022), URL: https://www.you-iggy.com/ja/type-of-substance/metal-salt/, 31 pages.

"Transition metal salt," You-iggy [online], May 20, 2022 (searched on May 25, 2022), URL: https://www.you-iggy.com/a/type-of-substance/transition-metal-salt/, 23 pages.

"Oxoacid salt," You-iggy [online], May 20, 2022 (searched on May 25, 2022), URL: https://www.you-iggy.com/ja/type-of-substance/oxoacid-salt/, 30 pages.

"Salt of oxoacid of group 6 element," You-iggy [online], May 20, 2022 (searched on May 25, 2022), URL: https://www.you-iggy.com/ja/type-of-substance/salt-of-oxoacid-of-group-6-element/, 14 pages.

"Type of substance," You-iggy [online], May 20, 2022 (searched on May 25, 2022), URL: https://www.you-iggy.com/ja type-of-substance/, 43 pages.

Safety Data, In accordance with Regulation (EC) No. 1907/2006, Revised on Dec. 2, 2013, version 6.6, Merck 106524 FDS '06, 11 pages.

Calmon et al., "Molybdenum 99 and environment," IRSN, Jun. 3, 2003, 13 pages.

\* cited by examiner

PREVENTIVE AND CURATIVE PEROXOMETALLATE BASED COMPOSITION, NOTABLY PHARMACEUTICAL COMPOSITION

CROSS-REFERENCE TO RELATED APPLICATIONS

This application is a continuation of U.S. Ser. No. 16/089,757 filed Sep. 28, 2018, which was a national stage application, filed under 35 U.S.C. § 371, of International Patent Application No. PCT/IB2017/051797 filed Mar. 29, 2017, which claims priority to FR 16 52697 filed Mar. 29, 2016. Each of the previously noted applications is hereby incorporated by reference in their entirety.

BACKGROUND OF INVENTION

Field of the Invention

The present invention relates to an active mixture in a therapeutic treatment, said mixture comprising a peroxometallate, such as for example a peroxomolybdate and/or, as for example a peroxolanthanate.

In particular, the present invention relates to an active mixture for the preventive and curative treatment of infections with Herpesviridae and in particular, infections with *Herpes simplex* 1 (HSV-1 or HHV-1) and with *Herpes simplex* 2 (HSV-2 or HHV-2). The present invention also relates to pharmaceutical compositions comprising such an active mixture, to preparation methods as well as to its uses, in particular within the scope of a therapeutic treatment.

Description of the Related Art

Among infectious pathologies, those due to viruses, in addition to their variable seriousness according to their types, which may range up to the death of the patient, and with a very uneven morbidity rate depending on the populations and on the times, pose a major therapeutic problem. This causal agent requires a cell host the metabolism and the constituents of which it uses for multiplying, whence the eradication difficulty by respectful treatment of the healthy tissue with respect to the infected one, or even a preventive treatment.

Among the viral infections which may affect humans, those with Herpesviridae are current, highly contagious and endemic. This family of viruses with DNA consists of eight types of viruses. Among them, HHV-1 or HSV-1 and HHV-2 or HSV-2 are responsible for orofacial-labial and vaginal-anal herpes.

All the herpes viruses, share clinical protein and genome structural properties like latency, recurrence or lytic activation. Like for all viral infections, the therapeutic means are complex and often limited. The invention is committed to solving the technical problem consisting in providing a pharmaceutical composition giving the possibility of acting against a viral infection, in particular a viral infection involving Herpesviridae and in particular HSV-1 and HSV-2.

Infections with HSV-1 and HSV-2 are very contagious (mainly by contact) and endemic (World Health Organization (WHO), January 2016, "The herpes virus", memorandum No. 400, http://www.who.int/mediacentre/factlsheets/fs400/fr/#. The reservoir is human, without any zoonosis or any vector. The prevalence of HSV-1 infections responsible for orofacial-labial herpes, of certain forms of genital herpes and of herpetic paronychia, is variable depending on the continents, the methods and the possibilities of diagnostics. It is estimated to be on average from 84 to 99% in Africa, from 50 to 100% in Asia, from 65 to 98% in Europe and from 57 to 68% in North America. The prevalence of infections with HSV-2, responsible for genital and anal herpes, is variable depending on the gender, the sociological and ethnic profile, the age and the continent. For example (according to: Centers for Disease Control and Prevention (CDC), 2010, MMW R Morb Mortal Wkly Rep., 59(15):456-459), seroprevalence in the United States for the age interval from 40 to 49 years old is estimated to be 32% in women and 20% in men.

By considering the morbidity rate, the HSV-1 and HSV-2 infections have a certain worldwide impact. Indeed, no totally efficient curative treatment exists in terms of eradications, whether the administration of antiviral drugs is per os or via a parenteral route, whether this is an analogue of pyrophosphate (foscarnet, for example), analogs of non-activatable or activatable nucleosides in situ (like fiacitabin, vidarabin, aciclovir and its prodrug valaciclovir, for example) or of an inhibitor of the helicase-primase enzymatic complex (pritelivir). They contribute to reducing the seriousness and the frequency of the symptoms but do not eradicate the infection. Most often, according to the low solubility of these molecules and in particular those of the «ciclovir» family (1.3 mg/mL in water at 25° C. for aciclovir) as well as of their limited intestinal absorption (of the order of 20% for aciclovir per os), consequent doses have to be administered to the patients.

Unlike ophthalmic topical drugs, the anti-HSV substances used in dermatology (such as ciclofovir, ibacitabin, aciclovir, for example) have clinical efficiency which remains modest and not constant.

Further, acquired forms of resistances to the virus of *Herpes simplex* to conventional treatments per os or via a parenteral route are described in emergence. They are most often connected to mutations of the viral genome (Bacon T. H. et al, 2003, Clin. Microbiol. Rev., 16(1), 114-128; Biswas S. et al, 2008, Antiviral Res., 80(1), 81-85).

In addition to the dimensions of infectivity, pain and a recurrent unesthetical aspect of the patient during the viral reactivation, these infections may become complicated by serious and complex pathologies although remaining quite rare, like herpetic encephalitis or keratitis. Maternal neonatal contamination may be 60% mortal in the absence of treatment. Herpetic infections and their development may be associated with other pathologies because of the immunodepression fact (either induced or pathological) or of immunosuppression of the patient such as for example, in the case of certain cancers or after a graft. HSV-2 is part of the most common infections (from 60 to 90%) among persons carrying the HIV. The risk of contracting a new HIV infection is multiplied by three in the presence of an HSV-2 infection. The carriers of both infections have a higher risk of transmitting the HIV.

Therefore the object of the invention is to solve the technical problem consisting in providing a method for preparing such a pharmaceutical composition.

The object of the invention is also to solve the technical problem consisting in providing a pharmaceutically active composition which is topically acceptable.

The object of the invention is also to solve the technical problem consisting in providing a pharmaceutically active composition which is easily soluble in hydrophilic solvents.

The object of the invention is further to solve the technical problem consisting in providing an active pharmaceutical composition during trans-epidermal passage.

The object of the invention is further to solve the technical problem consisting in providing a pharmaceutical composition which is deactivated during transcutaneous passage.

The object of the invention is further to solve the technical problem consisting in providing a pharmaceutical composition, the biophase of which is well delimited and attained.

The object of the invention is further to solve the technical problem consisting in providing a pharmaceutical composition for which the bioavailablity is minimum.

The object of the invention is further to solve the technical problem consisting in providing a pharmaceutically active composition having an anti-replication effect on a virus, and in particular on HSV.

The object of the invention is further to solve the technical problem consisting in providing a pharmaceutically active composition having high cytotoxicity for cells infected by a virus, and in particular by HSV.

The object of the invention is further to solve the technical problem consisting in providing a pharmaceutically active composition having little cytotoxicity for healthy cells.

The object of the invention is further to solve the technical problem consisting in providing a pharmaceutically active composition which has a prophylactic efficiency and in particular for HSV.

The object of the invention is further to solve the technical problem consisting in providing a pharmaceutically active composition which has a prophylactic efficiency notably during the prodromic phase of the infection and in particular for HSV.

The object of the invention is further to solve the technical problem consisting in providing a pharmaceutically active composition which has prophylactic efficiency notably by shortening the acute phase and in particular for HSV.

The object of the invention is further to solve the technical problem consisting in providing a pharmaceutically active composition which may prevent or limit the infectious process and in particular that of HSV.

The object of the invention is further to solve the technical problem consisting in providing a pharmaceutically active composition having good stability during its preservation at room temperature and up to 45° C.

BRIEF SUMMARY OF THE INVENTION

The inventors have discovered that it was possible to solve the technical problems mentioned above by providing a pharmaceutically or therapeutically active mixture comprising at least one peroxometallate.

By «pharmaceutically active» is meant the fact that the mixture or the composition has a beneficial activity within the scope of a therapeutic treatment.

The term of «mixture» refers to a composition and does not limit the composition which it designates to a particular preparation or manufacturing method. The term of «mixture» here gives the possibility of more easily distinguishing from a semantic point of view the «mixture» from the «composition» in particular when for example the «mixture» is integrated into a «composition» which comprises other ingredients.

The invention more particularly relates according to a first aspect, to a composition or mixture, preferably therapeutically active via a topical route, comprising:

at least one metal salt, the metal being selected from among molybdenum (Mo), tungsten (W), vanadium (V), gold (Au), a lanthanide, in particular lanthanum;
at least one chelating agent;
at least one source of peroxidizing radicals;
at least one buffering agent.

The invention concerns advantageously a composition or mixture, preferably therapeutically active by the topical route, comprising:

at least one metal salt, the metal being chosen from molybdenum (Mo), tungsten (W), vanadium (V), gold (Au), a lanthanide, in particular lanthanum;
at least one chelating agent;
at least one source of peroxidant radicals;
at least one buffer agent;
said mixture or composition preferably having a redox potential of 250 to 550 millivolts, and preferably 300 to 450 millivolts and again preferably 300 to 420 millivolts.

The mixture according to present invention advantageously gives the possibility of forming a drug, and more particularly a stable and active drug in situ.

The mixture according to present invention consists in an equilibrium of the aforementioned compounds advantageously forming a peroxometal complex including its salts. According to the inventors, without intending to be bound by theory, the mixture according to the present invention gives the possibility of forming a supermolecular structure of the lattice type in stable non-permanent equilibrium, which gives the possibility of providing at the extracellular level and in situ a catalyst for the Fenton and Haber-Weiss like reactions. These reactions are said to be «like» when they take place because of the metal of the mixture of the invention or of another metal which is not iron. A portion of the reactive substances generated extratemporaneously by the active substance penetrates the cell, and more advantageously the infected cell.

According to a variant the composition includes several metal salts, the metal being chosen from molybdenum (Mo), tungsten (W), vanadium (V), gold (Au), a lanthanide, in particular lanthanum.

Depending on the method of production, the metal salt is a molybdenum salt or one that contains molybdenum.

According to a method of production, the metal salt is a lanthanide salt or containing lanthanide.

According to a method of production, the metal salt is a mixture of molybdenum salt and lanthanide salt.

The invention concerns advantageously a composition or mixture, preferably therapeutically active by the topical route, comprising:

at least one molybdenum salt (Mo), optionally in combination with at least one salt of a metal chosen from tungsten (W), vanadium (V), gold (Au), a lanthanide, in particular lanthanum;
at least one chelating agent;
at least one source of peroxidant radicals;
at least one buffer agent;
said mixture or composition preferably having a redox potential of 250 to 550 millivolts, and preferably 300 to 450 millivolts and again preferably 300 to 420 millivolts.

Preferably, the metal salt is present as oxide(s) or peroxide(s) in the mixture. Advantageously, the metal oxides of the mixture of the invention give the possibility of forming an intermediate which is a metal acid, and more particularly a Lewis acid.

According to an alternative, a metal compound is preferred for which the state of oxidation of the metal is compatible with the Fenton-Haber-Weiss and Fenton-Haber-Weiss «like» reaction (an oxidation-reduction reaction which involves other metal ions such as iron, which, in our case, is in a context of chelation) metastable, i.e., mainly transition metals and in particular Mo(VI), W(IV) to (VI), V(III) to (V), Au(I) to (III).

According to an alternative, a lanthanide compound is preferred which may form a sesquioxide of the $LnO_3$ type, for which the state of oxidation is compatible with the metastable Fenton-Haber-Weiss and Fenton-Haber-Weiss «like» and particularly La(III), Ce(III) and (IV), Nd(III) and (IV), Sm(III) and (IV), Gd(IV).

Advantageously, the metal of the metallate or of the lanthanate has maximum valency.

Advantageously, the metal or the lanthanide is oxidized to its maximum degree of oxidation.

According to an preferred alternative, the metal salt comprises molybdenum. Thus, according to an alternative, the metal salt is a molybdenum salt. More specifically, the mixture according to present invention preferably comprises sodium molybdate. According to the invention, the use of a molybdenum salt is preferred, in which the valency of the molybdenum is of degree VI. This salt advantageously gives the possibility of providing significant stability to the mixture of the composition. Moreover, molybdenum, notably as a salt and for example as a sodium salt, with its reactive valency (VI), its compatible electronegativity, its very low cytotoxicity, its possibility of a Fenton-Haber-Weiss reaction which may be «like», is particularly preferred.

According to an alternative, the formed metal salt comprises a peroxometallate, and more particularly which may be found as a hydro-peroxometallate intermediate form.

Advantageously, the molybdenum salt is preferably with a peroxo or hydroperoxo unit. Still advantageously, the active substance is of the $MoO_4^{2-}$ type or its hydro-peroxo form (see Oyerinde Oyeyemi F. et al., Solution structure of molybdic acid from Raman spectroscopy and DFT analysis, Inorganica Chimica Acta 361 (2008) 1000-1007. Doi: 10.1016/j.ica.2007.06.025), for example, an intermediate complex of formula of the type $Na_4[Mo_2O_6(chelating)]$. $10H_2O$ in the mixture of the invention.

According to an alternative, the metal and its salt is a lanthanide or its salt.

According to an alternative, the formed metal salt comprises a peroxolanthanate, and more particularly which may be again found in the form of a hydro-peroxolanthanate intermediate. For example, it may be again found as an intermediate complex of a formula of the NaLn(chelating). $xH_2O_2.yH_2O$ type (with x and y which depends on the type of lanthanide (Ln) used in the mixture of the invention.

Advantageously, molybdenum and lanthanide salt, and more particularly lanthanum, is preferably of peroxo or hydroperoxo unit (see Suponitskiy, Y. L., Proshina, O. P., Dyunin, A. G. et al. Thermodynamic properties of lanthanum Molybdates, Russ. J. Phys. Chem. (2016) 90:267. Required: 10.1134/S00360244160202031X).

Advantageously, the use of a molybdenum salt gives the possibility of limiting the cytotoxicity of the mixture according to the invention, in particular on red corpuscles and lymphocytes, epithelia, fibroblasts, osteoblasts.

An advantage of the use of molybdenum lies in its natural presence as enzymatic cofactors (such as for example xanthin oxidase, glyceraldehyde-3-phosphate dehydrogenase with ferredoxin, etc.).

Advantageously, the use of a lanthanum salt gives the possibility of limiting the cytotoxicity of the mixture according to the invention.

According to a preferred alternative, the metal in the form of its active substance plays a role of a catalyst for the production of reactive substances $HO_2*$, and optionally $HO*$ and $O_2*$.

According to an alternative, the mixture according to the invention comprises from 0.1 to 500 µM, and preferably from 1 to 200 µM, and still preferably from 5 to 150 µM of metal salt.

According to an alternative, the mixture according to the invention comprises from 0.1 to 100 µM, and preferably from 1 to 50 µM, and further preferably from 5 to 30 µM of metal salt of molybdenum.

According to an alternative, the mixture according to the invention comprises from 0.1 to 100 µM, and preferably from 1 to 50 µM, and further preferably from 5 to 30 µM of metal salt of lanthanum.

The terms of «chelating agents» (or «chelatants») correspond to chemical compounds capable of forming a stable coordination complex with one or several ions and more particularly with the ionic forms of the metal present in the composition. The metal may be present in any form including in a peroxidized or hydroperoxidized form. This complex is said to be a «chelate».

The chelating agents may be suitable for the mixture according to the present invention advantageously should extracellularly catalyze, the in situ production of reactive radicals $HO_2*$ on the one hand; mainly but also $O_2*$ and $OH*$ and allow chelation of the calcium and metal ions including ferrous ions (Fe(II) or $Fe^{2+}$) and ferric ions (Fe(III) or $Fe^{3+}$) which are extracellular, bound or free. The release of these reagents is all the more efficient since the affinity of chelates for $Ca^{2+}$ and $Fe^{2+}/Fe^{3+}$ extracellular ions is significant. These chelates are stable compounds present in the pharmaceutically active mixture of the invention and participates in addition to the preferential production of the radical $HO_2*$, in the pharmaceutical or therapeutic activity of the mixture according to the present invention, notably by preferential chelation in situ of the calcium and iron ions. This chelation in situ would also allow regulation at an extracellular level of the cell calcium influxes, in particular induced by viral infection on the one hand, such as for example by Herpesviridae, and by the oxidative stress due to the presence of radicals or peroxocompounds on the other hand.

Advantageously, the chelating agents do not penetrate the cell and remain extracellular.

According to a preferred alternative, the chelating agents stabilized peroxo and hydro-peroxomolybdate complexes contained in the formulation. Such peroxo- and hydro-peroxomolybdates may be of the $(Mo_2O_6)^{4+}$ and $[Mo_4O_{12}(O_2)_2]^{4+}$ type.

Advantageously, according to an alternative, the chelating agent allows stabilization by chelation of the active substance ion $MoO_4^{2-}$, which in its sodium form has a molecular weight of 205,937 g per mole or peroxomolybdate (for example in the form of $MoO_3$-$BAPTAH_2^{2-}$ and/or $MoO_3$-$EGTAH_2^{2-}$).

According to an alternative, the mixture according to the invention comprises at least two chelating agents.

Advantageously, the chelating agent(s) bind(s) by coordination the oxidized or peroxidized metallate in solution.

According to an alternative, the chelating agent forms a complex with the oxidized or peroxidized metallate in order to form an intermediate dimer complex $[Mo_2O_6$ (chelatant)]$^{4+}$.10H$_2$O and/or of the peroxotetramolybdate (VI) form [Mo$_4$O$_{12}$(O$_2$)$_2$]$^{4+}$-Chelatant, when the metal salt is a molybdenum salt.

According to an alternative, the chelating agent forms a complex with the oxidized or peroxidized metallate in order to form a complex [W$_2$O$_6$(chelatant)]$^{4+}$.8H$_2$O, when the metal salt is a tungsten salt.

According to an alternative, the chelating agent forms a complex with an oxidized or peroxidized lanthanate in order to notably form a complex [La(O$_2$)-Chelatant]$^{2+}$. 6H$_2$O when the lanthanide salt is a lanthanum salt.

Advantageously, the chelating agent is compatible with steric capture of the oxidized and/or peroxidized complexes of the metallate. More particularly, the size of its N—N «pocket» which separates the carboxylic residues involved in the coordination as well as the steric folding of the carbonaceous chain of this pocket which should advantageously be compatible with the capture of intermediate metal complexes, notably in an oxidized peroxidized form. Advantageously, the chelating agent is compatible with the electronic charges of the metallate and with its external atomic orbital structure.

According to an aspect, the chelating agent(s) are selected from organic polyacids and salts thereof, notably amino-carboxylic polyacids. Typically, amino-carboxylic polyacids comprise one or several nitrogen atoms of an amine function preferably a secondary or tertiary amine bound to at least two carboxylic acid groups, via atoms, generally carbon and optionally oxygen atoms.

According to an alternative, the chelating agent(s) for example have at least three coordination groups, preferably carboxylic acid groups, at three ends of the molecule(s) forming the chelating agent(s), said coordination groups being separated by a chain of at least three atoms including at least one nitrogen atom.

Advantageously, the chelating agent(s) has(have) five coordination groups, preferably carboxylic acid groups, at five ends of the molecule(s) forming the chelating agent(s), said coordination groups being separated by a chain of at least six atoms and preferably nine atoms, including one nitrogen atom and preferably two nitrogen atoms separated by at least two atoms.

According to an alternative, the chelating agent(s) has (have) four coordination groups, preferably carboxylic acid groups, at four ends of the molecule(s) forming the chelating agent(s), said coordination groups being separated by a chain of at least six atoms and preferably twelve atoms, including two nitrogen atoms separated by at least eight atoms.

According to an alternative, the atoms separating said coordination groups and/or the nitrogen atoms of the chelating agent(s) are selected from carbon, nitrogen and oxygen atoms. Some of the atoms separating said coordination groups and/or the nitrogen atoms of the chelating agent(s) may be included in one or several identical or different atomic rings, such as for example non-aromatic, aromatic or heteroaromatic rings, for example a phenyl or a pyridyl.

Advantageously, the chelating agent is selected from among BAPTA (1,2-bis(o-aminophenoxy)ethane-N,N,N',N'-tetraacetic acid), EGTA: (ethylene glycol-bis (2-aminoethylether)-N,N,N',N'-tetraacetic acid)), DTPA (diethylenetriaminepentaacetic acid), and any of their mixtures According to an alternative, the chelating agent is selected from among BAPTA, EGTA and any of their mixtures.

Advantageously, BAPTA and/or EGTA allow better stability of the precursors as well as a better synthesis yield.

The pKas of the 4 carboxylic groups of BAPTA are: pK1 and pK2<4 (BAPTA insoluble), pK3=5.47, and pK4=6.36; and of EGTA are: pK1=2.00, pK2=2.65, pK3=8.85, and pK4=9.46.

Advantageously, the pKas of the chelating agent(s) are compatible with the pH of the inventive solution.

Advantageously, the pKas of the chelating agent(s) are compatibles with the pKa of the metal acid or metal peracid intermediately formed in the inventive solution.

Advantageously, the pKas of the chelating agent(s) are compatibles with the pH of the infected region, such as for example the epithelia.

Advantageously, the selected chelating agent(s) are slightly cytotoxic. This is notably the case of BAPTA and EGTA.

The metal salt and the chelating agents are present in a sufficient amount and ratio for producing {peroxo-metallate—chelating} agent(s)} complexes.

Preferably, at least one of the chelating agents present has a greater affinity for calcium than for the metal used in the mixture of the invention. This advantageously gives the possibility of substitution of the chelate complexes of the mixture of the invention with a chelating agent-calcium complex in vivo. Advantageously, the concentration of the chelate(s) is compatible with the concentration of the extracellular Ca$^{2+}$ (2-3 mM in a human plasma), i.e. the chelating agent(s) present in the mixture of the invention are in sufficient amounts for efficiently forming a complex from a therapeutic point of view with the present amount of extracellular calcium.

Advantageously, the chelate(s) present have greater affinity for iron (Fe$^{2+}$/Fe$^{3+}$) than for metal used in the mixture of the invention. This advantageously allows substitution of the chelate complexes of the mixture of the invention with a chelating agent-Fe$^{2+}$/Fe$^{3+}$ complex, in vivo.

According to an alternative, the mixture according to the invention comprises from 0.0001 to 1 mM of chelating agents.

According to an alternative, the mixture according to the invention comprises from 0.1 to 100 µM, and preferably from 1 to 50 µM, and still preferably from 5 to 20 µM of BAPTA. According to a variant, the mixture according to the invention includes from 1 to 80 µM, and preferably from 20 to 80 µM of BAPTA.

According to another alternative, the mixture of the invention comprises from 0.1 to 1 mM, and preferably from 50 to 800 µM, and still preferably from 200 to 700 µM of EGTA. According to a variant, the mixture of the invention includes 200 to 2,000 µM, and preferably 600 to 1,400 µM of EGTA.

According to another alternative, the mixture of the invention comprises BAPTA and EGTA present at a concentration from 0.0001 to 1 mM, and preferably from 5 to 20 µM and from 200 to 700 µM, respectively.

According to an alternative, the molybdenum salt and the chelating agents are present according to a ratio from 10/1 to 1/100 (ratio: Mo salt/chelating agent, expressed in molar concentrations).

According to an alternative, the lanthanum salt and the chelating agents are present according to a ratio from 10/1 to 1/100 (ratio: La salt/chelating agent, expressed in molar concentrations).

According to an alternative, the molybdenum salt and BAPTA are present according to a ratio from 3/1 to 1/10, expressed in molar concentrations.

According to an alternative, the molybdenum salt and EGTA are present according to a ratio from 1/10 to 1/70, expressed in molar concentrations.

According to an alternative, the lanthanum salt and BAPTA are present according to a ratio from 3/1 to 1/10, expressed in molar concentrations.

According to an alternative, the lanthanum salt and EGTA are present according to a ratio from 1/10 to 1/70, expressed in molar concentrations.

According to an alternative, the source of radicals is mainly $H_2O_2$.

According to an alternative, one or several secondary sources of radicals may be added or synthesized in minority in situ.

According to an alternative, $H_2O_2$ is an aqueous solution comprising $H_2O_2$ at 110 volumes or 30% or 8.82M.

Advantageously, the $H_2O_2$ source does not comprise any stabilizer selected from among: pyridine-carboxylic acids, such as for example picolinic acid; phosphonic and amino-phosphonic acids; substituted amides or amines; alkylsulfonic acids; and mixtures thereof.

According to an alternative, the main source of peroxidizing radicals is hydrogen peroxide. Thus, according to this alternative, the hydrogen peroxide is present at a concentration ranging from 200 to 600 mM, preferably from 300 to 500 mM, and further preferably from 340 to 450 mM.

According to an alternative, the mixture according to the invention comprises a hydrogen peroxide proportion ranging from 30 mM to 4.4 M, and preferably from 150 mM to 3 M, and preferably from 235 mM to 1.8 M, and still preferably from 260 mM to 440 mM. According to an alternative, the mixture of the invention does not comprise any extemporaneous addition of peracid.

Advantageously, the amount (or the concentration) of hydrogen peroxide ($H_2O_2$) is assayed by titration. Typically, it is possible to use an assay by means of a potassium permanganate solution.

The hydrogen peroxide concentration may also be assayed by UV spectroscopy.

Advantageously, a buffering agent is used for specifically controlling the pH of the mixture according to the invention.

Advantageously, a buffering agent is used in order to specifically control the pH during the application in situ of the solution according to the invention.

From among buffering agents, a carboxylic acid is preferred.

Preferably, the buffering agent does not comprise the following acids: hydroxylated carboxylic acids (par ex., malic acid) or polycarboxylic acids (par ex., citric and isocitric acids, malonic acid); carboxylic acids of a molecular weight greater than 100 g/mol and in particular long chain carboxylic acids (greater than $C_6$) because of the cell membrane destabilizations which they may induce, as well as unsaturated aliphatic carboxylic acids (sorbic acid, for example) because of their possibility of peroxidation of the alkenoic type which is cytotoxic.

According to an alternative, the present invention includes the presence of certain acids generated in situ during the synthesis, preferably in a small amount (such as for example peracetic acid). They are used as an accessory source of radicals upon the manufacturing of the invention and the therapeutic use of the invention.

According to an alternative, a buffering agent having a pKa at the physiological pH (skin and mucosas), i.e. a pH for example comprised between 4.4 and 5.0 and compatible with the pKa of the oxidized and/or peroxidized metal acid, the form of which is ionized (for ex. $MoO_4H_2$, pk1=3.61 and $pKa_2$=3.89) is preferred.

Preferably, the buffering agent is present in the mixture of the invention at a concentration comprised between 1 and 500 mM, and preferably between 10 and 200 mM, still preferably between 50 and 100 mM.

The ratio of the molar concentrations of hydrogen peroxide and of buffering agent is comprised between 2 and 9 and preferentially between 3 and 8.

Advantageously, the mixture is buffered in order to obtain a pH from 4.4 to 5.0 which is compatible i) for a contact of the invention with the skin and the mucous membranes, ii) the stability of the active substance $MoO_4^{2-}$ in the presence of $H_2O_2$, iii) the catalytic reaction of Fenton-Haber-Weiss «like» or not, and, iv) production in situ of radical species mainly of the type HOO*.

According to an alternative, the mixture comprises as a buffering agent allowing a pH from 4.0 to 5.2, preferentially from 4.4 to 5.0, for example a carboxylic acid, and preferably acetic acid.

Advantageously, the mixture has a redox potential from 350 to 450 mV, and preferably from 350 to 420 mV.

The redox efficiency of the mixture of the invention may also be estimated by oxidation in vitro of quercetin by iron(III) or $Fe^{3+}$ ions. It is notably possible to use for this a so-called «quercetin method» assay method, (adapted for example from studies of El Hajji H. et al (2006) "*Interactions of quercetin with iron and copper ions: Complexation and autoxidation*", Free Radic. Res., 40(3), 303-320 and Balcerzak M. et al (2008) "*Selective determination of Fe(III) in Fe(II) samples by UV-spectrophotometry with the aid of quercetin and morin*", Acta Pharm., 58, 327-334).

The present invention also relates to a method for preparing a mixture as defined according to the present invention. More specifically, the present invention relates to a method for preparing a mixture according to the invention which comprises (i) the preparation of a buffer solution (BS) comprising a buffering agent having an acid pH, (ii) the preparation of a solution of a metal complex (CS) comprising a metal oxide salt, (iii) the preparation of a first initial solution (Si1) comprising hydrogen peroxide, (iv) the preparation of a second initial solution (Si2) by mixing the solution BS with the solution Si1, (v) the preparation of a solution (S1) comprising a peroxo-metal compound by mixing the solution CS with the solution Si2, (vi) the preparation of a solution S2 by adjusting the pH of the solution S1 with a base, the pH of the solution S2 being more basic than the pH of the BS solution, (vii) the addition to the solution S2 of one or several chelating agents, (viii) optional adjustment of the pH, (ix) optional adjustment of the volume of the final solution, the obtaining of a pharmaceutically active mixture as defined according to the invention.

Depending on a variant, when two or more metal oxide salts are used, with different metal oxides, the preparation of a solution of a metal complex (SC) may consist of preparing separate solutions for each metal oxide salt and then mixing these solutions simultaneously or successively with the Si2 solution to prepare an S1 solution.

Preferably, the preparation of the mixture according to the present invention is achieved according to a catalytic synthesis method. The catalytic synthesis of the mixture according to the invention is typically sequential. Advantageously, the method of the invention comprises the sequence of steps (iii)=>(iv)=>(v)=>(vi)=>(vii)=>(viii)=>(ix).

Advantageously, the preparation method comprises a follow up by spectral analysis (for example by analysis of the IR, UV and/or visible spectra) at one or several of the preparation steps, and preferably during all the preparation steps.

According to an alternative, the first initial solution Si1 has a first redox potential greater than the redox potential of the mixture according to the invention.

Preferably, subsequently to step (ix), there is no dilution of the volume of the mixture so as to avoid displacements of the chemical equilibria of the mixture according to the present invention.

Of course it is advantageous to use substances or compounds with sufficiently satisfactory purity as raw materials. Notably it is necessary that the different substances or compounds have compatibility with therapeutic use.

According to an alternative, it is possible to conduct IR-FT, NMR-H and/or mass spectrometry on the produced mixture according to the invention in order to be sure of the compliance of the composition of the mixture with industrial requirements, and in particular for pharmaceutical therapeutic use. Also preferably an IR-FT spectrometry is conducted on the precursor components of the mixture of the invention.

According to an alternative, the pH may be controlled at one or several, or even the whole of the preparation steps.

According to an alternative, the redox potential may be controlled at one or several, or even the whole of the preparation steps.

According to an alternative, the mixture of the invention may be controlled by densimetry, and/or UV spectrophotometry, at one or several, or even the whole of the preparation steps.

According to an alternative, it is possible to assay the redox efficiency of the mixture of the invention by means of the quercetin method (UV spectrophotometric assay of the oxidation in vitro of quercetin by the $Fe^{3+}$ present or produced in vitro).

Advantageously, hydrogen peroxide is present in the Si1 solution at a concentration ranging from 200 to 600 mM, preferably from 300 to 500 mM, and still preferably from 330 to 460 mM.

According to an embodiment, the materiel used is metal and is preferably in stainless steel, optionally passivated metal.

According to an embodiment, the material may be re-passivated upon preparing the mixture of the invention for example by putting the material (which will be in contact with the mixture or its precursors) in contact with a hydrogen peroxide solution.

It is preferable to carry out an assay of the hydrogen peroxide source in order to ensure the amount of hydrogen peroxide present and to put it into play in the preparation of the mixture of the invention. This assay may be carried out for example by titration or by UV spectrophotometry (generally at 240 nm).

Advantageously, the pH of the buffering solution BS is from 4.4 to 5.0, and preferably from 4.7 to 4.8.

Advantageously, the buffering agent of the BS solution is a carboxylic acid/carboxylate buffer, and the BS solution has a hydrogen peroxide/carboxylate ratio comprised between 20/1 and 1/1, and preferably of about 5/1.

Advantageously, the ratio of acetic acid (AcOH) with its added acetate salt in a limiting amount, allows the lowest production of peracetic acid (AcOOH). Advantageously, in a preparation method according to the invention, the production of peracetic acid is minimum and the catalytic influence thereof is very small.

The preparation of the first initial solution Si1 comprises the preparation of an aqueous solution of carboxylic acid, and preferably of acetic acid and then addition of hydrogen peroxide.

Preferably, the first initial solution Si1 has a pH from 2.5 to 4.6, and preferably from 2.7 to 4.2. Advantageously, the first initial solution Si1 has a redox potential from 400 to 550 mV, and preferably from 420 to 500 mV.

Advantageously, the method comprises a measurement of the redox potential in steps (iii) to (ix), and preferably also comprises a measurement of the pH in steps (iii) to (ix).

According to an alternative, the second initial solution Si2 has a pH from 2.5 to 3.2, and preferably of about 2.9. According to an alternative, the initial solution Si2 has a redox potential greater than the redox potential of the first initial solution Si1. The redox potential of the second initial solution Si2 may be from 420 to 570 mV, and preferably from 440 to 520 mV.

According to an alternative, the buffering solution BS is introduced into the first initial solution Si1.

According to an embodiment, the hydrogen peroxide concentration in the second initial solution Si2 ranges from 300 to 500 mM, and preferably from 260 to 440 mM.

Advantageously, in the step (iv), the pH is maintained below the admissible pH limit for the catalytic synthesis reaction for the mixture according to the invention. A buffering agent is advantageously used in step (iv).

Advantageously, in the step (iv) the generated production in situ of peracetic acid is minimum.

Advantageously, in the step (iv) the redox potential of the Si1 solution of step (iii) is increased, for example by passing from a value of 440 to 460 mV to a value of 460 to 480 mV of step (iv).

By tracking the hydrogen peroxide concentration present during the preparation of the mixture of the invention, peroxide production is observed during its introduction, i.e. the putting of the hydrogen peroxide in contact with the buffering solution (step (iv)). Advantageously, the addition of hydrogen peroxide is achieved in an aqueous solution buffered beforehand to an acid pH. Thus, for the preparation of the first initial solution Si1, hydrogen peroxide is added into a solution with an acid pH, and for example with a pH from 2.7 to 4.2.

Advantageously, step (iv) leads to displacement of the equilibrium towards a production in situ of $H_2O_2$ with destruction of the possibly generated peracetic acid by the chemical equilibria.

According to an alternative, the buffering solution CS is introduced into the solution S1.

According to an alternative, the solution S1 comprising a peroxometal complex has a pH from 2.5 to 3.5, and preferably from 2.8 to 3.0.

According to an embodiment, the redox potential of the 51 solution comprising a peroxometal complex ranges from 400 to 550 mV, and preferably from 440 to 500 mV.

According to an embodiment, the hydrogen peroxide concentration in the solution S1 comprising a peroxometal complex ranges from 250 to 500 mM, and preferably from 320 to 450 mM.

In step (v), the added molybdate salt is in the form of molybdic acid $MoO_3.H_2O$ and $MoO_3.2H_2O$.

Under non-inventive conditions, the synthesis at the equilibrium of the active substance $MoO_4^2$, at room temperature, without any catalyst and without adding any strong acid ($H_2SO_4$, for example) would require several days.

According to an embodiment, the pH of the S2 solution is buffered to a value preferably comprised between 4.4 and 5.0, and for example from 4.5 to 5.0. Advantageously, at this buffered pH, it is the unstable form $MoO_4^{2-}$ which predominates (state of oxidation Mo(VI)) and hydrogen peroxide is stabilized. The hydrogen peroxide is often industrially stabilized by a phosphate buffer. An unstable intermediate compound of phosphomolybdate (yellow) may form which disappears at equilibrium, making $H_2O_2$ more reactive.

According to an alternative, the redox potential of the S2 solution ranges from 300 to 450 mV, and preferably from 360 to 410 mV.

The molybdenum Mo(VI) oxides in an aqueous solution and at the pH for synthesizing the mixture of the invention may exist under different molecular structures: $MoO_4^{2-}$ and $[MoO_6^2]$, $[Mo_2O_3(O_2)_4(H_2O)_2]^{2-}$, but also in reactive polynuclear forms (such as binuclear complex structures oxo-Mo(VI) (Dement'ev I. A. et al (2007) "Mononuclear, polynuclear, and cluster complexes of molybdenum and their reactions as models of biochemical systems and processes", Russ. J. Gen. Chem., 77(5), 822-843)).

Advantageously, the preparation conditions allow the formation in situ of peroxo-anD hydro-peroxomolybdate when the metal salt used is a molybdenum salt. The latter are of the: $[Mo_2O_3(O_2)_4(H_2O)_2]^{2-}$ type. According to an alternative, a molar excess of hydrogen peroxide of more than 1000 times, and of metal salt, and in particular of more than 10,000 times, and still preferably 15,000 times, relatively to Mo(VI) is preferred.

Advantageously, the chelating agent(s) as well the synthesis pH limit the displacements of the reaction of the «Jones reductor» type consisting in reduction of the metallate ion, advantageously i.e. molybdate, to a state of low oxidation corresponding to the metal molybdenum. According to an alternative, this displacement is limited in a slightly acid aqueous medium, typically with a pH comprised between 4.4 and 5.0, and for example from 4.5 to 4.7.

Preferably, when several chelating agents are present, independent solutions of chelating agents are prepared, each solution comprising a specific chelating agent.

According to a preferred alternative, the addition of the chelating agents is achieved with an order of increasing pKas.

For example it is possible to prepare a solution comprising a chelating agent of the BAPTA type on the one hand and a solution of a chelating agent of the EGTA type on the other hand. Preferably BAPTA is added and then EGTA.

Advantageously, the chelating agent(s) give the possibility in situ, i.e. after topical application notably, the Fenton-Haber-Weiss reaction with notably a dissociation constant $Kd_{chélate} \cdot Fe^{2+}/Fe^{3+} > Ca^{2+}$.

Advantageously, the chelating agent(s) extracellularly allow in situ, self-sustainment of the reactive radical production HOO* mainly and in minority $O_2$* and HO*.

According to an alternative, it is first possible to add BAPTA to the S2 solution in order to obtain a resulting S3 solution. The S3 solution for example has a pH ranging from 4.0 to 5.0, and preferably from 4.3 to 4.8. The S3 solution for example has a redox potential essentially identical to that of the S2 solution. In other words, the redox potential does not vary upon adding the chelating agent of the BAPTA type. According to an alternative, the redox potential of the S3 solution ranges from 250 to 450 mV, and preferably from 300 to 400 mV. Advantageously, preliminary dissolution of BAPTA in a small volume of S2 solution is achieved before putting it into contact with the remainder of the solution S2.

Preferably, the BAPTA concentration is in a molar ratio from 1/1 to 1/3 and preferably 1/2, relatively to the molybdenum salt.

For example, the S3 solution has a hydrogen peroxide concentration from 250 to 500 mM, and preferably from 320 to 440 mM.

Advantageously, it is possible to add at least one other chelating agent of the EGTA type into the solution S3 in order to obtain a resulting solution S4. According to an alternative, the S4 solution has a pH ranging from 4.0 to 5.0, and preferably from 4.3 to 4.7. According to an alternative, the redox potential of the solution ranges from 300 to 400 mV, and preferably from 350 to 390 mV.

Preferably, the concentration of the EGTA is in a molar ratio from 10/1 to 50/1 and preferably of about 25/1, relatively to the molybdenum salt.

For example, the S4 solution has a hydrogen peroxide concentration from 250 to 550 mM, and preferably from 320 to 470 mM.

According to an alternative, the pH in step (viii) is adjusted by a basic solution, for example of the sodium hydroxide type, preferably concentrated, for example to a concentration from 8 to 15 M. Advantageously, the pH in step (viii) may be adjusted to a value from 4.4 to 5.0, and preferably of about 4.6.

According to an alternative, the pH of the mixture of the invention ranges from 4.50 to 4.70. Advantageously, the redox potential of the mixture of the invention ranges from 320 to 390 mV.

According to a preferred alternative, the method comprises a reduction in the redox potential in step (vi). A reduction of the redox potential may for example be from 50 to 150 mV, and typically be of about 90 mV.

Preferably, the redox potential is substantially constant following the reduction of the redox potential of step (vi).

Advantageously, the mixture according to the present invention is stable overtime during storage, for example at room temperature or up to a temperature of 45° C. for six months. It is recommended to keep the mixture in darkness and away from humidity.

The pH is measured by means of a calibrated pH-meter and temperature compensated, with a combined electrode KCl 4M/AgCl The redox potential is measured with a combined pH-meter/redox-meter, equipped with a calibrated Platinum/calomel electrode. Typically, this measurement is performed at room temperature, i.e. 20° C. and at ambient pressure, i.e. 101325 Pa.

The hydrogen peroxide concentration is preferably evaluated in the aforementioned solutions by UV spectroscopy according to the equation derived from the Beer-Lambert law: $A_{240nm} = 43.6 \times l \times [H_2O_2]$ with l in centimeter and $[H_2O_2]$ in moles (Noble R. W. et al (1970) "The reaction of ferrous horseradish peroxidase with hydrogen peroxide", *J. Biol. Chem.*, 245(9), 2409-2413).

According to a specific alternative, the peroxo-metal compound of solution S1 is a peroxo-molybdenum compound.

The mixture of the invention therefore comprises according to this alternative a peroxometal compound. According to a preferred alternative, the mixture of the invention comprises a peroxomolybdenum complex.

According to an alternative, the solution comprises sodium molybdate in the Mo(VI) form. Advantageously, at the pH of the solutions of the invention, the salt is in a catalytic form $MoO_3$-$BAPTA^{3-}$ mainly and $MoO_3$-$EGTA^{3-}$ mainly, both sources of the active substance $MoO_4^{2-}$.

According to a particular embodiment, the mixture according to the invention comprises a salt, preferably of sodium, of molybdenum, a mixture of two chelating agents, preferably of the BAPTA and EGTA type, hydrogen peroxide and an acetate buffering agent (acetic acid/sodium acetate, for example).

According to a specific alternative, the mixture according to the present invention comprises:
Molybdate salt, and for example Sodium Molybdate;
BAPTA;
EGTA;
$H_2O_2$;
$CH_3COOH/CH_3COONa$;
$E_{redox}$ from 250 to 550 mV, and preferably from 300 to 450 mV, and again preferably from 300 to 420 mV;
pH 4.4-5.0.

According to a specific variant, the mixture according to the present invention includes:
Molybdate salt, and for example sodium Molybdate;
Lanthanum salt, and for example Lanthanum nitrate;
BAPTA;
EGTA;
$H_2O_2$;
CH3COOH/CH3COONa;
Erédox from 250 to 550 mV, and preferably from 300 to 450 mV, and again preferably from 300 to 420 mV;
pH 4.4-5.0.

Advantageously, the compounds of the mixture are in required amounts and pH conditions and redox potential conditions for forming a peroxomolybdate complex or hydro-peroxomolybdate complex wherein molybdenum is of valence VI.

According to a particular embodiment, the mixture of the invention comprises at least one chelating agent and at best and at least two chelating agents, and preferably at a concentration from 5 to 20 µM and 200 to 700 µM, respectively.

According to a particular embodiment, the mixture of the invention comprises 340 mM to 450 mM of main radical donor like $H_2O_2$.

The invention concerns in particular a composition according to the invention as a pharmaceutical composition, said composition comprising at least one metal salt, the metal being chosen from molybdenum (Mo), tungsten (W), vanadium (V), gold (Au), a lanthanide, in particular lanthanum; at least one chelating agent; and a source of peroxidant radicals. Such a composition according to the invention is useful in a therapeutic treatment method.

The invention also concerns a method of therapeutic treatment comprising administering, advantageously by topical application, to a subject in need of a therapeutically effective amount of a pharmaceutical composition according to the invention.

The invention also concerns a process for the preparation of a pharmaceutical composition according to the invention for use in a therapeutic treatment method.

The invention in particular relates to pharmaceutical compositions comprising or consisting of a mixture according to the invention.

The invention thus relates to a pharmaceutical composition for topical use, characterized in that it comprises a therapeutically active mixture, as defined according to the invention, or which may be obtained according to a method as defined according to the invention.

Advantageously, the pharmaceutical composition according to the invention comprises from 0.001 to 5 mM, preferably from 0.01 to 2 mM, and still preferably from 0.02 to 1 mM of the pharmaceutically active mixture.

The invention in particular relates to a pharmaceutical composition for topical use according to the invention for its use in a therapeutic treatment method for a viral infection, and in particular involving a virus of the Herpesviridae family.

The invention in particular relates to a pharmaceutical composition for topical use according to the invention for its use in a therapeutic treatment method for an infection involving HSV-1 and/or HSV-2.

The invention in particular relates to a pharmaceutical composition for topical use according to the invention for its use in an anti-inflammatory therapeutic treatment method.

The invention in particular relates to a pharmaceutical composition for topical use according to the invention for its use in a preventive or curative therapeutic treatment method.

The invention also relates to a pharmaceutical composition comprising molybdenum, at least one chelating agent and a source of peroxidizing radicals for its use in a method for therapeutic treatment of herpes. This composition is defined according to any of the embodiments, alternatives, advantages, preferences, or examples of the invention, taken alone or according to any of their combinations.

The term «according to the invention» makes reference to any of the embodiments, alternatives, advantages, preferences, or examples of the invention, taken alone or according to any of their combinations.

Typically, the pharmaceutical compositions for topical use according to the invention containing excipients and in particular excipients approved for the pharmacopeia.

By anti-infectious therapeutic treatment, is meant both a preventive therapeutic treatment, a prophylactic treatment and a curative treatment giving the possibility of for example limiting the infection in case of contaminating contact, the occurrence of a disease, its acute phase with, either partial eradication or not of the causal agent and/or limitation of its dissemination.

Advantageously, the active mixture or the pharmaceutical composition according to the present invention is active in situ during its application.

Advantageously, the active mixture or the pharmaceutical composition according to the present invention is active during trans-epithelial passage and preferably does not allow or only in a limited way its transcutaneous passage.

Advantageously, the active mixture or the pharmaceutical composition according to the present invention is deactivated during the transcutaneous passage.

According to an alternative, the mixture according to the invention or a composition comprising it is applied via a topical route at the orofacial level.

According to an alternative, the mixture according to the invention or a composition comprising it is applied via a topical route at the genital or anal level.

According to an alternative, the mixture according to the invention or a composition comprising it is applied via a topical route on the skin.

According to an alternative, the mixture according to the invention or a composition comprising it is applied via a topical route on a mucosa.

According to an alternative, excipients approved by European pharmacopeias (Ph. Eur.), National pharmacopeias (USP, JP, IP, Ph. Helv., Ph. Belg., Ph Fr., BP, DAB, ÖAB, notably) and international pharmacopeias (Ph. Int.; WHO), may be introduced during the manufacturing of the invention and/or into the "mixture" noted as "Mixture 1".

The mixtures and compositions of the invention are particularly suitable for pharmaceutical activity in human beings.

Advantageously, the active mixture of the invention gives the possibility of applying reactions of the Fenton-Haber- Weiss type and Fenton-Haber-Weiss «like» type, and of preferentially generating the radical $HO_2*$ and in minority the radicals $O_2*$, $HO*$.

According to the inventors, the permeation of the reactive substance HOO*, is sufficient for inducing in a limited and controlled way cell apoptosis.

According to the inventors, the permeation of the reactive substance HOO*, is sufficient for having in an efficient and controlled way a viral anti-replication effect.

According to the invention, the redox potential of the mixture of the invention is preferably used for limiting within a narrow scope, the concentrations of the precursors of the radical active substances so as to generate a sound equilibrium between: an anti-replication effect/moderate cytotoxicity for the healthy cell/significant cytotoxicity for the infected cell/an infection preventive effect.

Advantageously, the therapeutically or pharmaceutically active mixture according to the invention gives the possibility of mainly and preferentially generating the reactive radical species HOO*.

Thus, according to the present invention, the extracellular calcium in vivo is the main triggering factor for the production of HOO*. For example this is mainly an action at the complex $2Mo_{(VI)}$-$BAPTA_2(H_2O_2)$ when the molybdenum salt and BAPTA are set into play in the mixture of the invention. For example, this is mainly an action at the complex $2Mo_{(VI)}$-$EGTA_2(H_2O_2)$ when the molybdenum salt and EGTA are set into play in the mixture of the invention.

Advantageously, the production in the extracellular medium of HOO* allows extracellular modifications (oxidations of extra-membrane amino acid residues for example) which may thus limit the viral infection by modifying cell recognition.

Advantageously, the production in the extracellular medium of HOO* as well as its cell permeation are compatible with its long lifetime ($\geq 1$ s) and its great cell penetration vs. OH* or $O_2*$ (1 ms and penetration of the order of 1 nm). Advantageously, this substance HOO* is involved in the Haber-Weiss reaction and the Fenton reaction («like» or not) at the extracellular and intracellular level and allows self-sustainment of the latter.

Advantageously, the mixture containing Mo(IV) according to the present invention has a pH from 4.4 to 5.0. This notably allows optimization of the rate constant $k_{obs}$ ($M^{-1} \cdot s^{-1}$) of the $HO_2*/O_2*$ decomposition.

Advantageously, the modification of the intracellular redox potential by contacting with the composition according to the invention allows an apoptotic/anti-apoptotic equilibrium. More particularly, this apoptotic/anti-apoptotic equilibrium notably depends on the existence of an infection by HSV and mainly by HSV-1 and -2.

According to an alternative, the mixture of the invention is selectively active on cells infected by HSV and mainly by HSV-1 and -2.

Thus, there exists a close equilibrium between the routes of the stress induced by the HSV infection, including the calcium influx and the regulation of apoptosis.

This equilibrium is perturbed by the presence of intracytoplasm radicals and of the modifications of the cell redox potential. This induces the same cellular stress routes as an infection by HSV, the same calcium influxes and the same inductions of metabolic routes, these same routes being back-regulated towards another anti-apoptotic equilibrium. This supports the therapeutic effect of the mixture according to the invention or of compositions comprising it.

According to an alternative, the pharmaceutical composition or the mixture of the invention is used in a therapeutic treatment method for a labial and orofacial herpes.

According to an alternative, the pharmaceutical composition or the mixture according to the invention is used in a therapeutic treatment method of a genital and anal herpes.

According to an embodiment, the active mixture according to the invention has an anti-infectious efficiency (moderate-to-low direct action on the virus, viral receptors at the cell as possible candidates), anti-recognition and internalization (significant action, cell receptors to the virus). These efficiencies are external to the cell and limit the viral infectivity. Thus, the active mixture according to the invention has a prophylactic action. Thereby again, the active mixture according to the invention has an anti-infectious efficiency.

According to an alternative, the pharmaceutical composition or the mixture according to the invention is used in a therapeutic treatment of a population expressing HSV in its enveloped, replicative or infectious.

According to an alternative, the pharmaceutical composition according to the invention or the mixture is used in a therapeutic treatment of a cell population or of a tissue expressing HSV-1 (Kessler H. H. et al (2000) "Detection of Herpes Simplex Virus DNA by real-time PCR", J Clin Microbiol., 38(7), 2638-2642).

According to an alternative, the pharmaceutical composition according to the invention or the mixture is used in a therapeutic treatment of a cell population or of a tissue expressing HSV-2 (Kessler H. H. et al (2000) "*Detection of Herpes Simplex* Virus DNA by real-time PCR", J Clin Microbiol., 38(7), 2638-2642).

Advantageously, the active mixture according to the invention has an anti-replication effectiveness induced from the fact of a preliminary contact to the infection with a healthy cell or tissue. The active mixture according to the invention may be used for preventing an infection by limiting intracellular viral replication and/or by limiting the penetration of the virus into the cell.

Advantageously, the active mixture according to the invention has a preferential anti-replication efficiency on cell metabolism of the infected cell (oxidative stress routes and calcium channels). The active mixture according to the invention may be specifically used for directly acting against the intracellular viral replication and against a cell overinfection by HSV-1 and/or HSV-2 of the same infected tissue or of a healthy tissue close to the previous one.

According to an alternative, the active mixture according to the invention heterogeneously induces an inhibition of the production of interleukin-6 (IL-6) of a human cutaneous flap and thus has an anti-inflammatory efficiency.

DETAILED DESCRIPTION OF THE PREFERRED EMBODIMENTS

Figure 1:
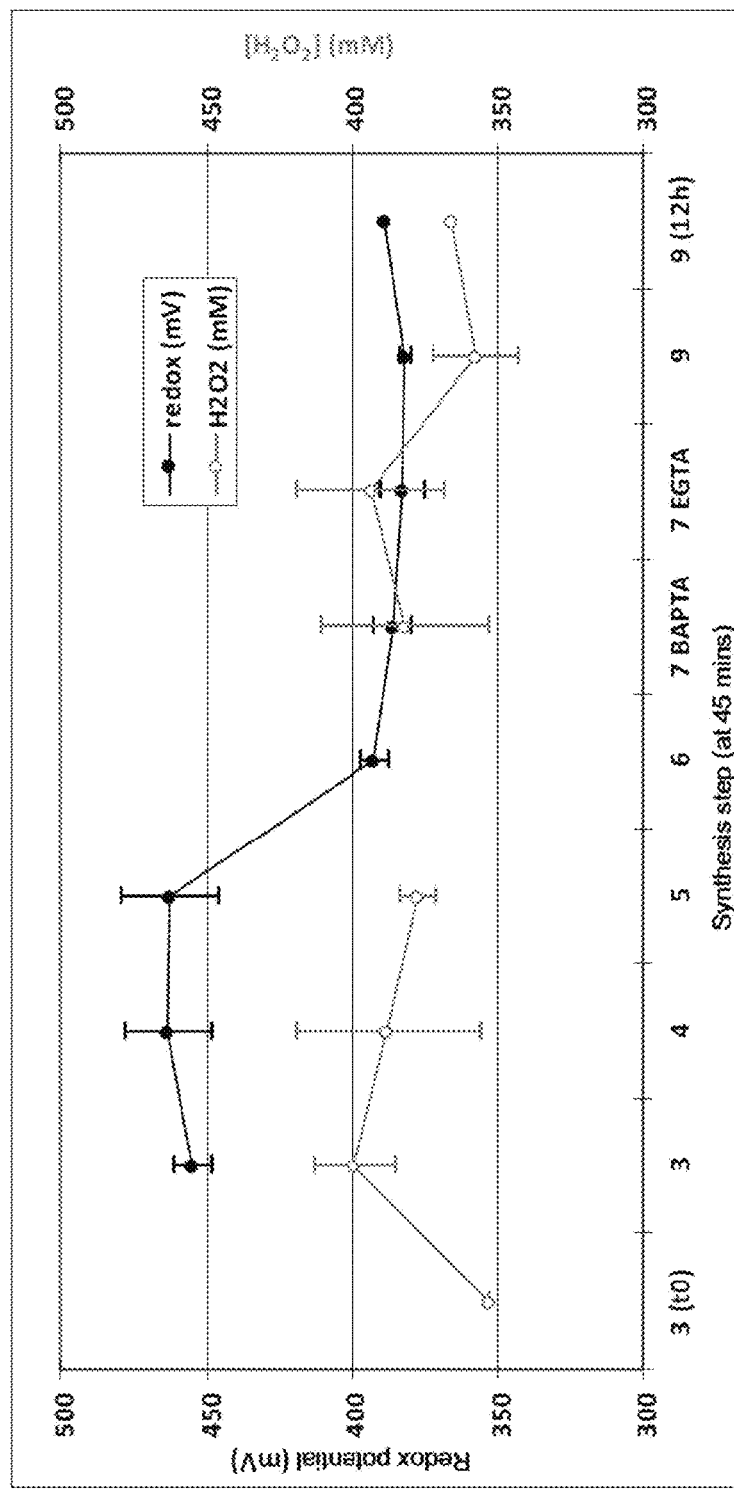
FIG. 1 represents the variations of the redox potential and of the $H_2O_2$ concentration during the preparation of the Mixture 1.

Example 1—Example of an Active Mixture According to the Invention

The present example is made with a molybdenum salt. A composition of a formula according to table 1 ("Mixture 1"), expressed in the initial concentration of the constituents is prepared:

TABLE 1

| Components | Mixture according to the invention |
|---|---|
| Sodium molybdate | 20.7 μM |
| BAPTA | 12.6 μM |
| EGTA | 526 μM |
| $H_2O_2$ | 353 mM |
| $CH_3COOH/CH_3COONa$ | 70 mM |
| Ph (with NaOH) | 4.4-5.0 |
| $E°_{redox}$ | 300 to 420 Mv |

The composition is said to be an «initial» composition since it corresponds to the concentrations of the added reagents without taking into account the applied catalytic process.

All the constituents used for the synthesis as well as the finished product are validated by their IR-FT spectrum.

TABLE 1a

| Product | Purity | Raw formula | CAS No. |
|---|---|---|---|
| Sodium molybdate dihydrate | 98-103% | $Na_2MoO_4 \cdot 2H_2O$ | 10102-40-6 |
| BAPTA: (1,2-bis(o-aminophenoxy)ethane-N,N,N',N'-tetraacetic acid) | ≥98% | $C_{22}H_{24}N_2O_{10}$ | 85233-19-8 |
| EGTA: (ethylene glycol-bis(2-aminoethylether)-N,N,N',N'-tetraacetic acid) | ≥99% | $C_{14}H_{24}N_2O_{10}$ | 67-42-5 |
| Hydrogen peroxide | 29-31% | $H_2O_2$ | 722-84-1 |
| Glacial acetic acid | 99.8-100.5% | $CH_3COOH$ | 64-19-7 |
| Sodium acetate trihydrate | 99-101% | $C_2H_3NaO_2 \cdot 3H_2O$ | 5010524 |
| Sodium hydroxide | 10N | NaOH | 1310-73-2 |
| Demineralized water | 1 μS | $H_2O$ | 7732-18-5 |

The figures of the measurements carried out during and after the synthesis are the averages from the 3 productions.

The amounts indicated below are for the preparation of one liter of Mixture 1.

A—STEP (i): Preparation of the Buffering Solution (Solution BS)

| | |
|---|---|
| $CH_3COOH$ (100%; δ: 1.05 g · cm$^{-3}$ (liquid, 20 C.)) | 4.0 ml (final 70 mM) |
| $CH_3COONa \cdot 3H_2O$ (100%) | 8 g (final 59 mM) |
| Water | qsp 1 L |
| Verification of the pH: | 4.7-4.8 |
| Room temperature (20° C.) | |

B—STEP (ii): Preparation of the Metal Complex Solution (Solution CS)

| | |
|---|---|
| $Na_2MoO_4 \cdot 2H_2O$ (source of Mo(VI); 100%) | 200 mg (final 2.4 mM) |
| Water | qsp 340 ml |
| Mild stirring, room temperature | |

C—STEP (iii): Preparation of the Initial Solution (Si1)

| | |
|---|---|
| Water | 900 mL |
| $CH_3COOH$ (100%) | 4 mL (70 mM) |
| Add very slowly and with very mild stirring (250 rpm), pH: 2.9-3.8 $E_{redox}$: 470-490 mV and then, | |
| $H_2O_2$ (30%) | qsp for final 1.2% by weight and according to the preliminary assays |
| At 45 mins: | |
| pH: 2.70-2.90 $E_{redox}$: 440-460 mV By the Noble equation: $[H_2O_2]$ = 380-410 mM | (Solution Si1) |

D—STEP (iv): Preparation of the Initial Solution (Si2)

| | |
|---|---|
| Introduce the « BS solution » into the solution Si1 12 mL (≈1 mM acetate) Add with mild stirring. At 45 mins: | |
| pH: ≈2.90 $E_{redox}$: 460-480 mV By the Noble equation: $[H_2O_2]$ = 360-410 mM | (Solution Si2) |

E—STEP (v): Preparation of the Peroxomolybdenum Solution S1

| Introduce the « CS solution » into the solution Si2 | 10 mL |
|---|---|
| At 45 mins: | |
| pH: 2.80-3.00 | |
| $E_{redox}$: 450-480 mV | |
| By the Noble equation: $[H_2O_2]$ = 370-400 mM | (Solution S1) |

F—STEP (vi): Preparation of the Solution S2

| Adjustment of the pH with mild stirring: | |
|---|---|
| NaOH 9.9-10.1M | 3.6 mL for = 0.9 L of the mixture 1 |
| pH 4.5-5.0 | |
| At 45 mins: | |
| pH: 4.60 | |
| $E_{redox}$: 380-390 mV | (Solution S2) |

G—STEP (vii): Addition of the Chelating Agents—Preparation of the Solution S4

| Introduction of BAPTA (98.8%) | 6 mg/L, |
|---|---|
| after very slow dissolution of BAPTA with mild stirring in an aliquot of the formulation S2 (1.4 L) equilibrated beforehand at 25° C. (the so called « S3.1 » solution). Pool of the solution S3.1 with the solution S2 in order to form the solution S3.2. | |
| At 45 mins: | |
| pH: 4.40-4.70 | |
| $E_{redox}$: 380-390 mV | |
| By the Noble equation: $[H_2O_2]$ = 370-390 mM | |
| Introduction of EGTA (99.1%) | 200 mg/L in the solution S3.2 in order to form the solution S4 |
| Dissolve with mild stirring. | |
| At 45 mins: | |
| pH: 4.40-4.60 | |
| $E_{redox}$: 380-390 mV | |
| By the Noble equation: $[H_2O_2]$ = 370-420 mM | |

H—STEP (viii): Adjustment of the pH

Adjustment of the pH (NaOH 9.9-10.1M, i.e. ≈400 g/L)=>pH: 4.60±0.2

I—STEP (ix): Adjustment of the Volume for the Final Solution (FS)

| Adjustment of the volume with demineralized water | qsp 1 liter |
|---|---|
| At 12-18 hours: | |
| pH: 4.50-4.70 | |
| $E_{redox}$: 380-390 mV | |
| By the Noble equation: $[H_2O_2]$ = 350-380 mM | |
| By titration: $[H_2O_2]$ = 400-430 mM | |
| Density: δ = 1.004 g/ml | |

The mixture according to the invention, ready to use, is stable in darkness for more than 6 months at room temperature or at 45° C.

Na hydro-peroxo-molybdate is at a concentration of 24.3 µM in the final Mixture 1.

Example 2—Signature by Variation of the Redox Potential

The signature of the active mixture according to the present invention is evaluated by the variation of the redox potential during the synthesis of a composition prepared according to Example 1.

According to FIG. 1, relatively to the initial solution (≈470 mV; step 3), reduction of the redox potential of ≈90 mV (≈380 mV) in step 6 (adjustment of the pH with soda). The redox potential remains constant until the end of the synthesis (step 9). The same applies during the ageing of the formulations of the invention according to example 1 over 6 months at room temperature (389 mV±5 mV) and at 45° C. (389 mV±8 mV) for a pH of 4.56±0.40 and 4.53±0.41, respectively.

Example 3—Signature by Consumption and Production of $H_2O_2$—Generation of the Peroxo-Reagent Equilibrium and of the Redox Potential of Mixture 1

The signature of the active mixture according to the present invention is evaluated by consumption and production of $H_2O_2$ during the synthesis of a composition prepared according to example 1.

According to FIG. 1, relatively to the $H_2O_2$ concentration of the initial solution (353 mM; step 3 to 10), a sudden peroxide production (≈42 mM; including a small fraction of peracetic acid) is observed because of the addition of $H_2O_2$ into the buffering solution (acetic acid/acetate). If the addition of $H_2O_2$ is not carried out in an aqueous solution acid-buffered beforehand (step 3; pH=2.84±0.1), its spontaneous and rapid degradation would result from this because of a too high pH (water) ($pKa_{HO2^*-/O2^*-}$: 4.8).

From step 4 up to step 7, a limited consumption of $H_2O_2$ is observed (10 mM±6 mM), until its stabilization at 381 mM±5 mM (step 7; +BAPTA).

The addition of EGTA displaces the peroxide equilibrium (Fenton «like» reaction) by peroxide degradation, i.e. 393 mM±29 mM in step 7, to 357 mM±26 mM in step 9, and 365 mM±15 mM in step 9+12 hours.

In step 6, a sudden drop in the redox potential is observed (from 463 mV±15 mV to 392 mV±17 mV) by adjustment of the pH is observed. The addition (step 7) of the chelating agents BAPTA and then EGTA successively contributes to stabilization of the redox potential (386 mV±5 mV and 383 mV±6 mV) by stabilization of the chemical equilibria.

Example 4—Assay of the Redox Efficiency of the Mixture of the Invention: Quercetin Methods A—the Reactive Solutions 1—Quercetin A solution of quercetin dihydrate (2-(3,4-dihydroxyphenyl)-3,5,7-trihydroxy-4H-1-benzopyran-4-one dihydrate, 3,3',4',5,7-pentahydroxyflavone dihydrate; ($C_{15}H_{10}O_7 \cdot 2H_2O$) at $10^{-3}$ mol/L is prepared in methanol.

2—Hydrochloric Solution

A first solution of hydrochloric acid 1M is prepared in methanol. A second solution is prepared at 0.3 M in methanol. The reactive solution is prepared by adding 343 µl of the solution 1M to 1,357 µl of the 0.3 M solution.

3—Solutions of $Fe^{3+}$ (Reference Abacus)

A solution of $Fe^{3+}$ ($Fe_2(SO_4)_3 \cdot xH_2O$) at 2 mg/ml is prepared in HPLC water. It is then diluted in order to obtain eight reference solutions at: 20, 100, 200, 300, 400, 500, 1,000 and 1,500 µg/ml. These solutions are finally diluted 20 times in human plasma or in HPLC water in order to finally obtain the concentrations of: 0, 1, 5, 10, 15, 20, 25, 50 and 75 µg/ml.

4—Solutions of $Fe^{2+}$ (reference abacus, activity control)

A solution of $Fe^{2+}$ ($FeSO_4 \cdot 7H_2O$) at 89 mg/ml is prepared in HPLC water. It is then diluted in order to obtain three reference solutions at: 0.445, 4.45 and 44.5 mg/ml. These solutions are finally diluted 10 times in HPLC water in order to finally obtain concentrations of: 0, 0.0445, 0.445 and 4.45 mg/ml.

B—Assays with the Quercetin Method

The presence of $Fe^{3+}$ (abacus) or its production ($Fe^{2+}$ abacus and efficiency of the mixture of the invention after 2 mins of contact) are quantified by the quercetin method.

According to the conditions of analysis or use of the Mixture 1:

"mixture$_{ox}$" refers to the mixture according to the invention as an oxidizer.

"mixture$_{red}$" refers to the mixture according to the invention as a reducing agent.

The $Fe^{3+}$ productions are the following:

| |
|---|
| Transferrin-2$Fe^{3+}$ + mixture$_{red}$ + 3$H^+$ → Transferrin$_{red}$ + 2$Fe^{3+}_{(aq)}$ + mixture$_{ox}$     (1) |
| $Fe^{3+}_{(aq)}$ + mixture$_{red}$ + $e^-$ ⇌ $Fe^{2+}_{(aq)}$ + mixture$_{ox}$     (2) |
| $Fe^{3+}_{(aq)}$ + quercetin$_{red}$ → quercetin$_{ox}$ + $Fe^{2+}_{(aq)}$     (3) |

The reaction (1) is in a plasma medium.

The reaction (2) is in a plasma medium or in HPLC water and corresponds to the equilibrium of the Fenton-Haber-Weiss reaction.

The reaction (3) is the oxidation reaction of quercetin for evaluating the redox potential of the Mixture 1.

In an acid medium and at 70° C., quercetin is specifically oxidized by ferric iron ($Fe^{3+}$; El Hajji et al 2006 and Balcerzak et al, 2008) borne by the transferrin in a plasma medium and not by ferrous iron ($Fe^{2+}$). The $Fe^{3+}$ ion is soluble under these conditions.

30 µl of the quercetin solution are added to 170 µl of the hydrochloric reactive solution. After homogeneization, 50 µl of the sample ($Fe^{3+}$ in human plasma or in HPLC water, $Fe^{2+}$ in HPLC water, the mixture of the invention after 2 mins of contact with human plasma) are added. The solutions are intensively stirred and shortly and then incubated for 1 h at 70° C. After incubation, the samples are centrifuged for 15 min. at 14,000 rpm and at room temperature. A 100 µl of supernatants are sampled. The UV spectrum of each sample is acquired from 230 to 500 nm. The blanks: water, $Fe^{2+}$, $Fe^{3+}$, plasma are subtracted according to the type of experiment. The absorption peak of oxidized quercetin by the produced Fe from plasma transferrin and the Fenton-Haber-Weiss reaction in situ is retained (from 285-305 nm).

The apex of the curve is centered towards 292 nm when the experiment is carried out in HPLC water or in plasma. It may be moved by a maximum of 10 nm when the experimental blanks are subtracted.

1—$Fe^{3+}$ Abacus

An abacus for the Fe(III) ion is produced for example by measuring the UV absorbance (on the range 250-330 nm) of oxidized quercetin for different concentrations of $Fe^{3+}$ (cf. the $Fe^{3+}$ range above) in human plasma, and by reporting the optical density versus the wavelength.

From the spectrum of the region 250-330 nm, the area under the curve (AUC) between 285 and 305 nm is calculated with the formula:

$$AUC_{285nm}^{305nm} = \int_{285nm}^{305nm} f(x)\, dx = \int_{285nm}^{305nm} \text{Absorbance} \cdot d(\lambda)$$

Accordingly, each area of the surface of the peak 285-305 nm for each point of the range of $Fe^{3+}$ is plotted for graphic illustration. The tendency curve is plotted (Excel), the equation (the correlation coefficient $R^2$ for which the closest value to 1 validates the experiment) is deducted (Excel).

Figure 2:
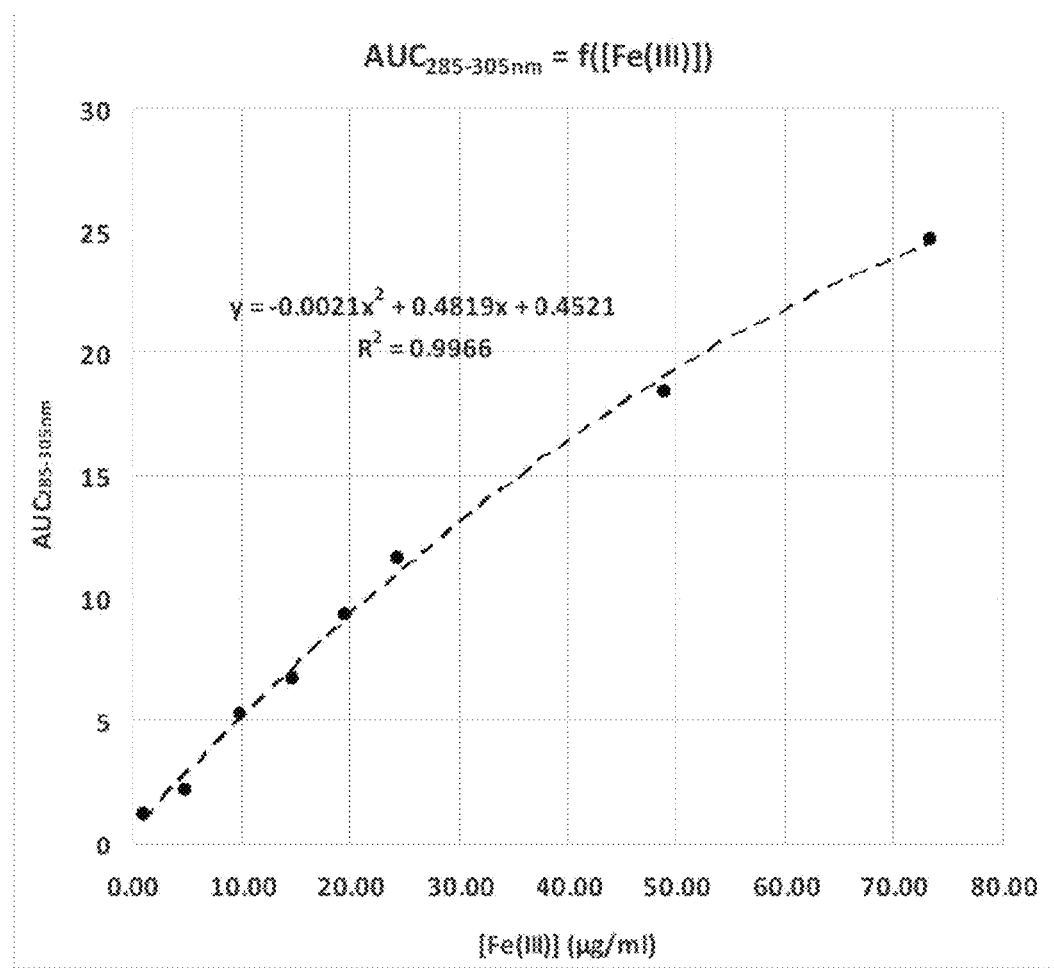
FIG. 2 illustrates an $Fe^{3+}$ abacus used for assaying the redox efficiency of the Mixture 1.

It may be a linear or polynomial form of the type: $y = ax^2 + bx + c$. By experiment, this relationship may be of the type $y = -0.0021x^2 + 0.4819x + 0.4521$; $R^2 = 0.9966$ (FIG. 2). (4)

For a mixture according to the invention, the concentration of Fe equivalent produced in a plasma medium or from $Fe^{2+}$ is the reflection of the oxidizing potential of the invention and is calculated from equation (4). This is an indirect method for measuring the redox efficiency of the Mixture 1 by assaying in UV light the oxidized quercetin by $Fe^{3+}$. Accordingly, a concentration in $Fe^{3+}$ «equivalent» mentioned. Also, it is possible to compare the redox potential of a solution according to the invention to be tested, relatively to a reference solution according to the invention, in other words making a comparison with the quantification of the redox efficiency of a mixture according to the invention.

2—$Fe^{2+}$ Abacus

In the same way as for the ion Fe(III), an abacus is produced for the Fe(II) ion is produced. For example, the UV absorbance (230-500 nm) of the quercetin peak oxidized by the $Fe^{3+}$ obtained from the mixture of the invention at 1.22 µM of active substance (250 µg/L) and 2 mins of contact with $Fe^{2+}$ is for example measured for the range described above. The same mathematical analyses of AUC as described for the Fe(III) ion may be conducted.

3—Assay of the Redox Efficiency of the Mixture of the Invention for Example at 1.22 µM (250 µg/L) of Active Substance $MoO_4^{2-}$.

According to the procedure described in B–, the redox efficiency of a mixture according to the invention (1.22 µM of $MoO_4^{2-}$ in human plasma) is tested for: i) evaluating its ageing at room temperature and at 45° C., ii) validating its production and comparative evaluating the formulations, iii) quantifying its transcutaneous passage, iv) its bioavailability and, v) its biophase.

According to the equation (4), the specific area of the UV absorbance peak is calculated (as an AUC) between 285 and 305 nm of the quercetin peak oxidized by the free $Fe^{3+}$ produced after plasma contact for 2 mins of the mixture of the invention (equations (1), (2) and (3)) at a final concentration finale of 1.22 µM with the transferrin-$Fe^{3+}$ complex. On average, the production of Fe equivalent ($Fe^{3+}_{eq}$) is of the order of 30 to 50 µg/ml of plasma.

4—Estimation Abacus in a Plasma Medium of the Effective Concentration of the Mixture According to the Invention Plasma iron is not free. It is bound to transferrin (or siderophilin) in its ferric form ($Fe^{3+}$) in amount of 1 to 2 residues per molecule. Iron in its ferrous form ($Fe^{2+}$) is not circulating outside its complexation with hemoglobin. It is considered that the human plasma used is not hemolyzed. The quercetin reaction of the inventive mixture with plasma copper is considered as negligible.

Figure 3:
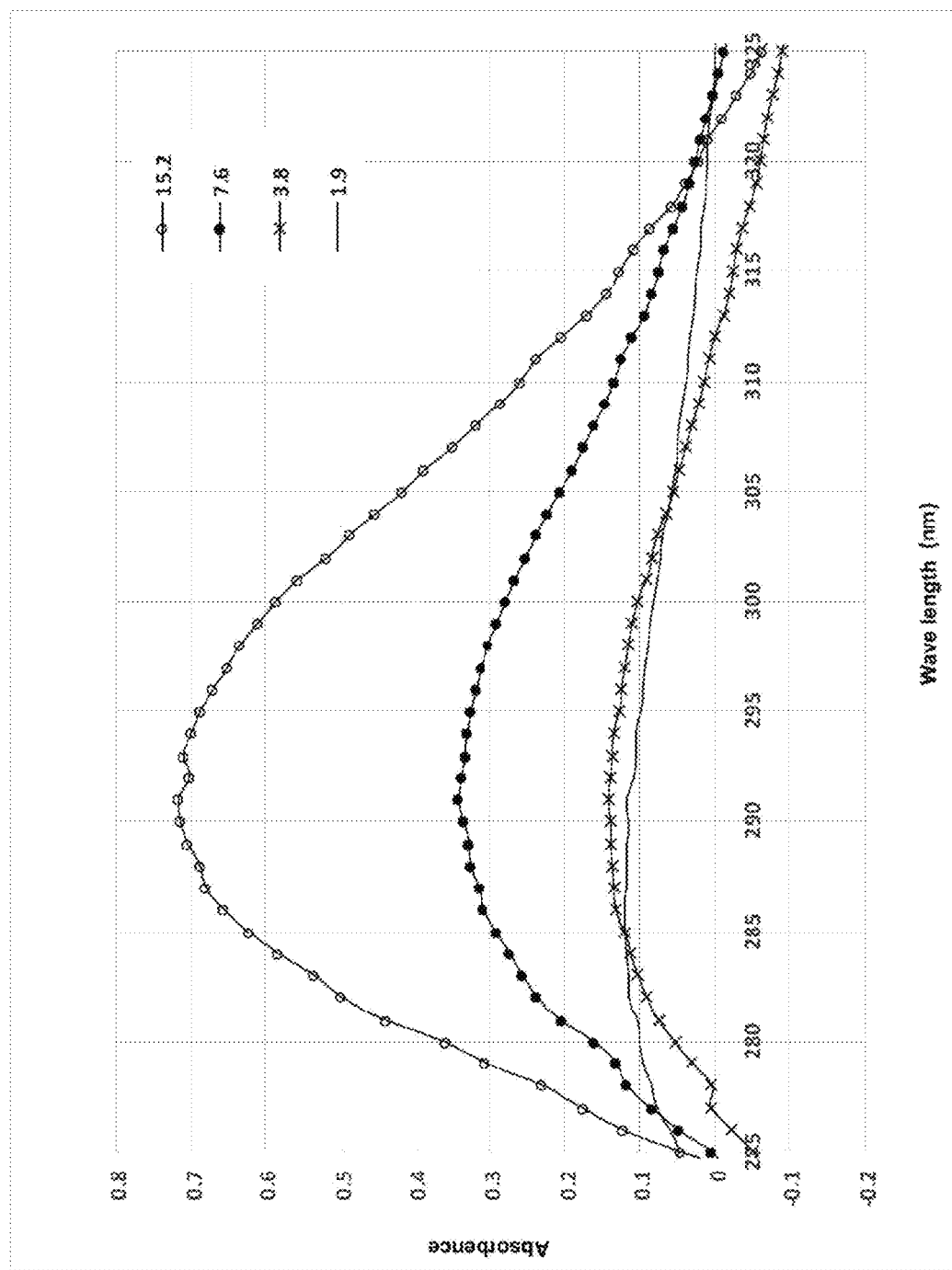
FIG. 3 is an illustration of the redox efficiency of the Mixture 1 at different concentrations thereof (absorbance of quercetin by Fe(III) in a human plasma medium after contact (2 mins) with the Mixture 1 (in nM $MoO_4^{2-}$).

A range of concentrations of the mixture of the invention (15.2, 7.6, 3.8 and 1.9 nM of final $MoO_4^{2-}$) was incubated in human plasma. The reaction with quercetin was conducted as described in B–. The specific absorption peak (subtraction of the plasma blank+quercetin) was integrated as described in B-1 (FIG. 3).

Figure 4:
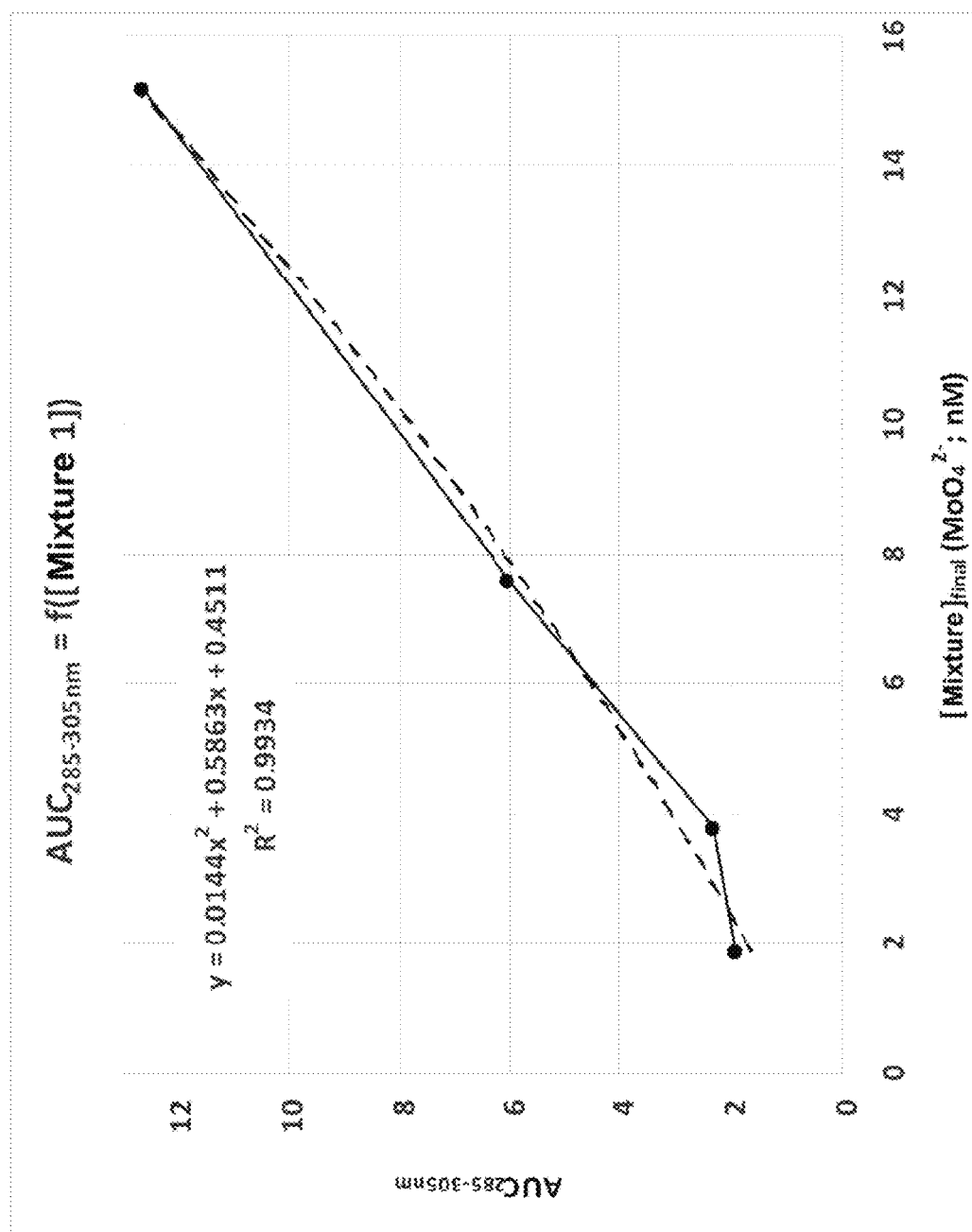
FIG. 4 illustrates an abacus of the redox efficiency of the Mixture 1 at different concentrations of the latter.

The abacus was plotted (Excel) in a polynomial scale and the tendency equation was calculated ($y=0.0144x^2+0.5863x+0.4511$ with $R^2=0.9934$ (5); FIG. 4).

A proportionality relationship (equation 5) is ascertained between the amount of the invention in an added concentration to human plasma and the amount of equivalent of $Fe^{3+}$ (equation 4) detected by oxidation reaction of quercetin, i.e. 28.95, 12.19, 3.97, 3.12 µg of $Fe^{3+}_{eq}$/mL of human plasma, according to the range of the mixture of the invention described above.

Example 5—Evaluation of the Oxidation-Reduction Efficiency of the Invention on Human Plasma After adding the Mixture according to the invention (Example 1—Mixture 1") to human plasma and after a contact time of 2 mins, up to a concentration of 0.03038 µM of $MoO_4^{2-}$, the oxidation reaction of quercetin for the production of $Fe^{3+}$ issued from the plasma transferrin-$Fe^{3+}$ complex and the Fenton-Haber-Weiss reaction is optimum and linear (cf. example 4).

Figure 5:
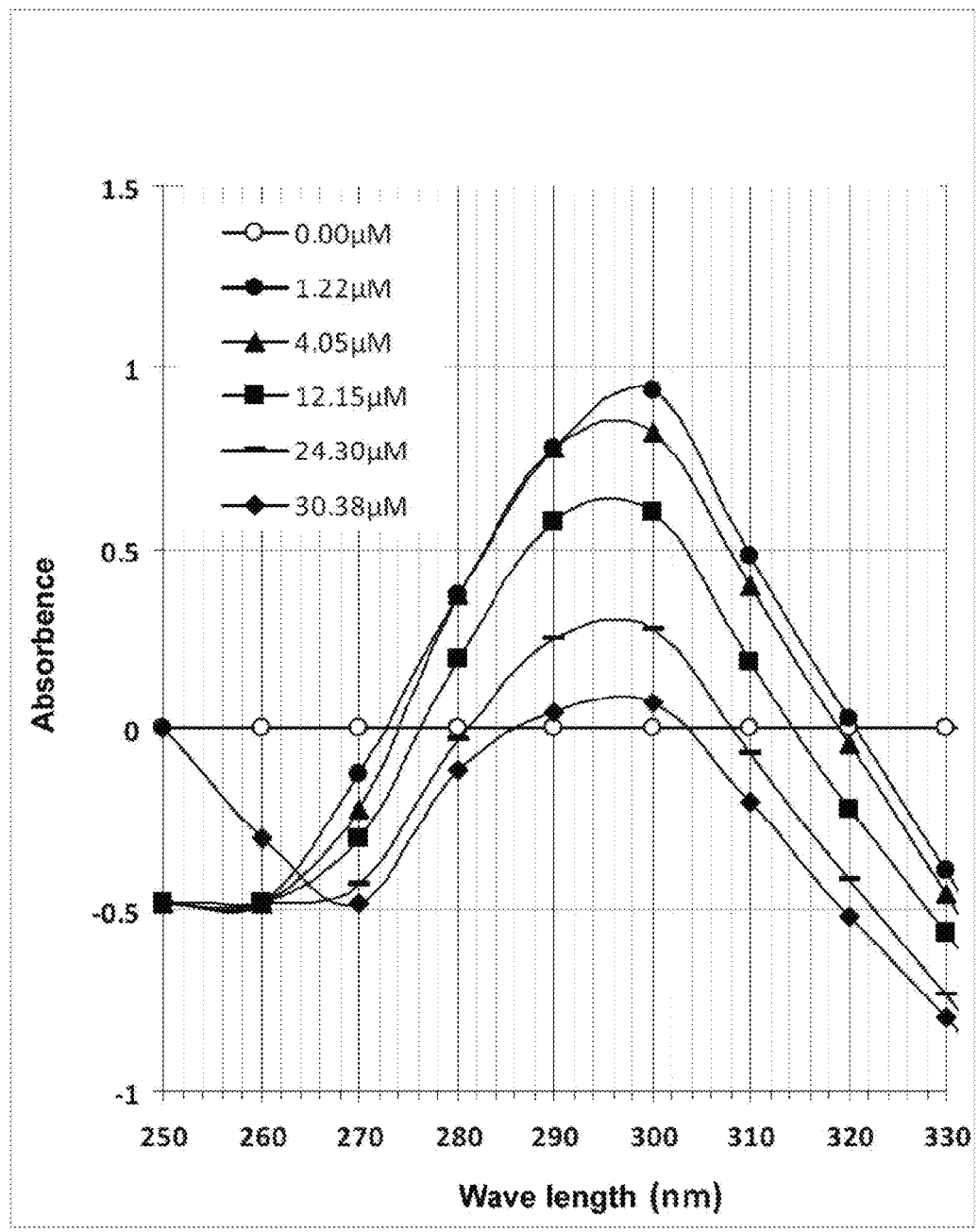
FIG. 5 illustrates the influence of the Mixture 1 at different concentration of $MoO_4^{2-}$ on the production in situ in human plasma of $Fe^{3+}$, i) stemming from the transferrin-$Fe^{3+}$ complex after contacting with the formulation, ii) on the $Fe^{2+}/Fe^{3+}$ equilibrium and, iii) on the oxidation of quercetin.

After subtraction of the experimental blanks, an increase in the concentration of the invention generates a reduction in the production in situ of quercetin oxidized by $Fe^{3+}$ because of the displacement of the equilibria of the Fenton-Haber-Weiss reaction ($Fe^{3+}$ $Fe^{2+}$). The final tested concentrations of $MoO_4^{2-}$ were then 0.00, 1.22, 4.05, 12.15, 24.30 and 30.38 µM (FIG. 5).

Example 6—Anti-Replication Efficiency

A—The models

Four contact models of the mixture according to example 1 ("Mixture 1") were tested. They represent the four physiological possibilities that the Mixture 1 may be encountered during a topical therapeutic application, i.e.:

Model 1: Mixture 1 on cells infected with HSV-1,
Model 2: Mixture 1 on cells not yet infected with HSV-1,
Model 3: Mixture 1 on cells not yet infected and Mixture 1 on HSV-1 free (not yet infectious),
Model 4: Mixture 1 on HSV-1 before infection.

Two contact times of the Mixture 1 were tested, i.e. 2 mins or 1.5 mins, and then removal of the Mixture 1.

Two concentrations of the Mixture 1 were tested: 0.81 and 2.03 µM of active substance, i.e. 167 and 417 µg/L, respectively.

The method for quantifying the efficiencies is qPCR (quantitative Polymerase Chain Reaction; Mullis K. et al (1986) "*Specific Enzymatic Amplification of DNA In Vitro: The Polymerase Chain Reaction*"; *Cold Spring Harb. Symp. Quant. Biol.*, 51 (Pt 1), 263-273.)

The anti-replication efficiency (AE) of the Mixture 1 on HSV 1 was evaluated in qPCR with specific primers of the viral genome (Kessler H. H. et al (2000) "*Detection of Herpes simplex virus DNA by real-time PCR*" *J. Clin. Microbiol.*, 38(7), 2638-2642).

The cytotoxicity of the Mixture 1 (C) on the BHK-21 line was evaluated in qPCR with specific primers of the gene of the small ribosomal sub-unit 18S (Texcell—Evry, France).

The multiplicity of infection (MOI): 1, i.e. $5.10^5$ $TCID_{50}$ (Tissue Culture Infective Dose 50%).

The qPCR experiments were conducted at t0 h (2 h after contact between BHK-21 and HSV-1, and then removal of HSV-1), t2 h-, t4 h- and t8 h-post-infection.

The AE/C ratio gives us the Efficiency Index in vitro (EI) of the Mixture 1 corresponding to a study model.

Model 1:

BHK-21+HSV-1 (2 h; infection)=>washing (PBS) for viral removal=>samples t0 h=>+Mixture 1 (2 min.)=>washing (culture medium) for removing Mixture 1=>cell incubation at 37° C.=>samples t2 h-, t4 h- and t8 h-post-infection.

Model 2:

BHK-21+Mixture 1 (1.5 and 2 mins)=>washing (PBS) for removing the Mixture 1=>cells+HSV-1 (2 h; infection)=>washing (culture medium) for removing HSV-1=>samples t0 h=>cell incubation at 37° C.=>samples t2 h-, t4 h- and t8 h-post-infection.

Model 3:

BHK-21+Mixture 1 (1.5 and 2 mins)=>washing (PBS) for removing Mixture 1.

HSV-1+Mixture 1 (1.5 and 2 mins)=>washing (PBS) for removing Mixture 1.

Pool of the cells and of the viruses having been in preliminary contact with Mixture 1 (2 h; infection)=>washing (culture medium) for removing HSV-1=>samples t0 h=>cell incubation at 37° C.=>samples t2 h-, t4 h- and t8 h-post-infection.

Model 4:

HSV-1+Mixture 1 (2 mins)=>washing (PBS) for removing the Mixture 1=>+BHK-21 (2 h; infection)=>washing (culture medium) for removing HSV-1=>samples t0 h=>cell incubation at 37° C.=>samples t2 h-, t4 h- and t8 h-post-infection.

B—Results

TABLE 2

Reduction to 8 hours of the multiplication of HSV-1 in BHK-21 cells after contact with Mixture 1 (in μg/L of active substance) or of acyclovir (ACV); Efficiency Index in vitro (EI).

| Substance | Reduction of the HSV-1 replication at t8h (%)* | | | | | EI at t8h / model** | | | | |
|---|---|---|---|---|---|---|---|---|---|---|
| | Mixture 1 | | ACV | Mixture 1 | | Mixture 1 | | ACV | Mixture 1 | |
| Contact time (min.) | 2 | 2 | 2 | 1.5 | 1.5 | 2 | 2 | 2 | 1.5 | 1.5 |
| Concentration (μg/L) | 167 | 417 | $10^3$ | 167 | 417 | 167 | 417 | $10^3$ | 167 | 417 |
| Model 1 | −97 | −98 | −12 | NT | NT | 37 | 48 | 2 | NT | NT |
| Model 2 | −72 | −96 | −1 | −70 | −86 | 4 | 23 | 1 | 3 | 7 |
| Model 3 | −93 | −97 | −6 | −78 | −90 | 14 | 35 | 1 | 4 | 10 |
| Model 4 | −56 | −69 | −52# | NT | NT | 2 | 3 | 2# | NT | NT |

*The reduction of the HSV replication (RR) by the tested substances (Mixture 1, control acyclovir) is expressed as a percentage and corresponds to the qPCR quantifications ratio of the HSV-1 genomes and of the cytotoxicity which is evaluated by quantifying the sub-unit 18S of the host cell: RR = $\{(100 \times ([HSV-1]_{test}/[18S]_{test}))/([HSV-1]_{control+}/[18S]_{control+})\} - 100$.
**The anti-replication Efficiency Index in vitro (EI) of the tested substances is represented by the $([HSV-1]/[18S]$ evaluated in specific qPCR) of the positive control infected by HSV $([HSV-1]_{control+}/[18S]_{control+})$ vs. that of the tested substances (Mixture 1, control acyclovir): EI = $([HSV-1]_{control+}/[18S]_{control+}/([HSV-1]_{test}/[18S]_{test})$.
[ACV]: 1 g/L The best EIs (Table 2) are obtained after 2 minutes of contact of the mixture 1 and of a concentration at 417 μg/L. We note a significant influence of the contact time on the EIs (1.5 mins and 2 mins; models 2 and 3).

The EIs obtained with the models 1 and 3 with a contact time of 2 mins and a concentration of the mixture 1 of 167 μg/L, are particularly significant.

Regardless of the model, the EIs obtained with acyclovir ("ACV") are not significant (Table 2).

For Model 1 (Mixture 1 on Infected Cells):
The best EI (Table 2) with two concentrations of the mixture 1 (2 mins of contact, 167 and 417 μg/L, EI: 37 and 48, respectively).
The Mixture 1 has direct efficiency (Tables 2 and 3) on intranuclear viral replication, on cell metabolism probably.
The Mixture 1 has good specificity of the infected cell (Table 3, tests 4 and 5; model 1 vs. 2).

TABLE 3

Quantification percentages by qPCR (gene 18S or HSV; at 8 h post-contact of 2 mins): i) of the multiplication of the BHK-21 line (control: non-infected line) and, ii) of the replication of HSV-1 (control: infected line).

| Gene/genome | 18S (%) | | | | | | HSV (%) | | |
|---|---|---|---|---|---|---|---|---|---|
| Control | Line + (PBS − HSV) | | | Line + (PBS + HSV) | | | | | |
| Test substance | Mixture 1 | | | Mixture 1 | | | Mixture 1 | | |
| [active substance] | 167 μg/L | 417 μg/L | ACV (mg/L) | 167 μg/L | 417 μg/L | ACV (mg/L) | 167 μg/L | 417 μg/L | ACV (mg/L) |
| Model 1 | 45 | 27 | 108 (1) | 49 | 30 | 118 (1) | 1 | <1 | 76 (1) |
| Model 2 | 62 | 41 | 57 (1) | 68 | 44 | 62 (1) | 19 | 2 | 61 (1) |
| Model 3 | 118 | 70 | 111 (1) | 98 | 58 | 92 (1) | 7 | 2 | 86 (1) |
| Model 4 | 120 | 107 | 97 | 139 | 123 | 111 | 64 | 38 | 54 |
| Tests | 1 | 2 | 3 | 4 | 5 | 6 | 7 | 8 | 9 |

For the Mixture 1 (at 167 to 417 μg/L) or ACV (at 1 or $10^3$ mg/L), regardless of the control used (line+PBS−HSV or line+PBS+HSV), the quantification results of 18S are comparable for a same model (Table 3, test 1 vs. 4, 2 vs. 5, 3 vs. 6).

For the Mixture 1, a dose-dependence remarkable anti-replication efficiency (Table 3, tests 7 and 8) is ascertained for the models 1, 2 and 3. This is not observed for ACV (Table 3, test 9).

A comparable cytotoxicity of the Mixture 1 (167 μg/L) and of ACV (1 mg/L) (Table 3) is noted according to the models 2 and 3 (Table 3, tests 1, 3, 4 and 6).

An absence of anti-HSV efficiency (Table 2 and Table 3, test 9) for ACV (1 mg/L or 1 g/L) is noted. The models introduced for the study of the Mixture 1 cannot correspond to a study dealing with ACV.

For the Model 2 (Mixture 1 on a Cell Before Infection):
An interesting EI (Table 2; contact for 2 mins and 417 μg/L, EI: 23).
The Mixture 1 has an action on the cell which becomes less receptive to the infection and/or acquires a metabolism incompatible with the replication of the virus (Table 3, tests 7 and 8).

For the Model 3 (Mixture 1 on: Non-Infected Cell and HSV-1, Separately and Before the Pool):
An interesting EI (Table 2) with two concentrations of the mixture 1 (2 mins of contact, 167 and 417 μg/L, EI: 14 and 35, respectively).
Depending on the applied dose (167 or 417 μg/L) zero cytotoxicity (Table 3, test 4) or limited cytotoxicity (Table 3, test 5) for very good antiviral efficiency (Table 3, tests 7 and 8, respectively).

We have an efficiency of the mixture 1 which would be an accumulation of the model 2 with a significant action on the cell and of the model 4 with a limited action on the virus alone (Tables 2 and 3).

For the Model 4 (Mixture 1 on HSV-1):

A low EI (contact time: 2 mins, 167 and 417 µg/L, EI: 2 and 3, respectively; Table 2) which is confirmed by absence of cytotoxicity but significant viral replication (Table 3, tests 8 and 9).

C—Conclusions

On the BHK-21 line, the main efficiencies of the Mixture 1 is: i) of having a preferential cytotoxicity of the infected cell, ii) of inhibiting the viral replication in the infected cell and, iii) limiting the infection of the healthy cell.

The target may be a membrane (receptors for the virus, for example) and/or metabolic (regulation of the stress and apoptotic routes, for example).

Viral Recognition and Internalization

According to model 4, the Mixture 1 has a low direct anti-replication efficiency at the virus. Under these experimental conditions, close to the topical therapeutical use, this observation is in favor of a limited alteration of the viral receptors to the cell: gB (HSV-2), gC (HSV-1), gD and gH/gL (HSV-1 and -2). The Mixture 1 would only alter in a limited way the viral glycoproteins by its in vitro Fenton-Haber-Weiss reaction.

Similarly, we do not note the significant influence of the Mixture 1 on the phospholipid membrane of HSV which may perturb the membrane fusion and penetration.

Under these experimental condition ns, Mixture 1 is not a virucide.

Viral Replication and Cell Metabolism:

The qPCR technique uses the cell lyzate at 8 h post-infection. A reduction in the viral replication may result from poor recognition and/or internalization and/or replication (modification of the cell metabolism induced by the infection and/or the Mixture 1).

If the viral desalting route was altered by the Mixture 1 without altering the other routes and regardless of the model, the resulting EIs would be much smaller because of the cytoplasm accumulation of virions.

According to model 2 (EI: 23 with 2 mins of contact time and 417 µg/L), low viral replication after preliminary cell contact with the Mixture 1 (Table 2 and Table 3, test 8) is observed.

According to this model, the BHK-21 cell was in contact at 2 mins with Mixture 1. The contact time with HSV in a complete and nutritive culture medium was 2 hours. The Mixture 1 induced cell modifications having a lifetime lasting for more than 2 hours and further predicting prophylactic efficiency of Mixture 1.

In addition to the recognition of HSV-1 by the cell being partly affected by the Mixture 1 because of its probable and limited action on the viral glycoprotein gD (38% of replication; Table 2), this recognition may also be affected by an action on the cell receptors to gD (HVEM and nectin) as well as on the two other surface cell receptors to gB and gH/gL which are heparane sulfates and integrins.

Because of radical permeation (modification of the intracellular or transmembrane redox potential, regulation of the oxidative stress routes), the cell calcium influxes may be moved. These cell calcium influxes are also induced by the HSV infection. However the latter may be demobilized immediately because of the introduction into the Mixture 1 of free and non-permeating chelating agents (limitation of the cell cytotoxicity). Other major cell modifications on the other hand should not be excluded and may correspond to protein oxidations or reductions (cysteinyl bridges, for example) and in particular of structural proteins which may occur in viral endocytosis.

According to model 3 (Table 2 and Table 3, tests 7 and 8), a significant reduction in the viral replication is observed (EI: 14 and 35 for 2 mins of contact time, 167 and 417 µg/L, respectively).

Both phenomena accumulate. The first is a limited action at the virus (cf. model 4), the second more significant (cf. model 2) is at the cell.

The addition of the EIs of models 2 and 4 (2 mins and 417 µg/L), i.e. 23 and 3, respectively, gives a sum (26) less than but close to the experimentally obtained one for model 3, i.e. 35.

A potentialized accumulation i) of poor recognition of the HSV partners and cell is contemplated and ii) an inhibited internalization and/or replication notably by alteration of the cell metabolism.

Model 1 (EI: 48 with 2 mins of contact time and 417 µg/L) is the most performing.

The action of the anti-infectious Mixture 1 is preferential on the cell than on the virus. This action is all the more performing since the cell is infected beforehand.

In this model which corresponds to the best therapeutic problem, it is obvious that the Mixture 1 has a specific major intracellular pharmacological efficiency. For 417 µg/L of active substance, the table 3 shows that the amount of ribosomal sub-units 18S is less (depending on the control used, 27 and 30%, tests 2 and 5) in this model than in the model 2 (depending on the control used, 41 and 44%, tests 2 and 5) and in the model 3 (depending on the control used, 70 and 58%, tests 2 and 5) which is an argument for the specificity of the infected cell vs. the healthy cell.

The targets of the Mixture 1 in this model cannot be either the recognition or the internalization, but actually metabolic modifications. The latter are placed in a new equilibrium, notably because of the transmembrane radical passage, the modification of the redox potential of the cell and the presence of outer chelating agents, between the oxidative stress routes (already induced by the infection), the calcium fluxes (already induced by the infection), the inhibition of the calcium-dependent release of the virions, the modifications by oxidation of proteins directly or indirectly involved in viral replication.

Example 7—Evaluation Ex Vivo of the Production of Interleukins

Non-pathological biopsies (8 biopsies and 4 donors) of human skin issued from surgical operations for reducing weight were treated ex vivo with the Mixture 1 (5 mg/L of active substance; 2 mins). The supernatants in which the biopsies were found were sampled at 6 h and 24 h post-contact in order to quantify the interferons-α (IFN-α; inhibition of the infection with HSV; Mikloska Z. et al (2001) "*Alpha and Gamma Interferons Inhibit Herpes Simplex Virus Type 1 Infection and Spread in Epidermal Cells after Axonal Transmission*", J. Virol., 75(23), 11821-11826), -β(IFN-β; inhibition of HSV replication; Sainz Jr. B. et al (2002) "*Alpha/Beta Interferon and Gamma Interferon Synergize To Inhibit the Replication of Herpes Simplex Virus Type 1*", J. Virol., 76(22), 11541-11550) and interleukin 6 (IL-6; inflammation marker).

The positive experimental control is a physiological solute (NaCl 100 mM).

No modification of the cell base level of IFN-α and IFN-β was noted.

Depending on the biopsies and on the donors and accordingly on the trauma of the surgical operation and of the experimental manipulation:

At 6 h post-contact (FIGS. 6 and 7):
with NaCl as a control, production of basal IL-6 of 277 pg/mL±11 to 2,866 pg/mL±206.
with Mixture 1, inhibition of the IL-6 production relatively to the NaCl control, from 0 pg/mL to 1,015 pg/mL±17.

At 24 h post-contact (FIGS. 6 and 7):
with NaCl control, basal IL-6 production of 1,485 pg/mL±37 to 7,454 pg/mL±199.
with Mixture 1, inhibition of the IL-6 production relatively to the NaCl control, of 84 pg/mL±15 to 5,910 pg/mL±29.

Figure 6:
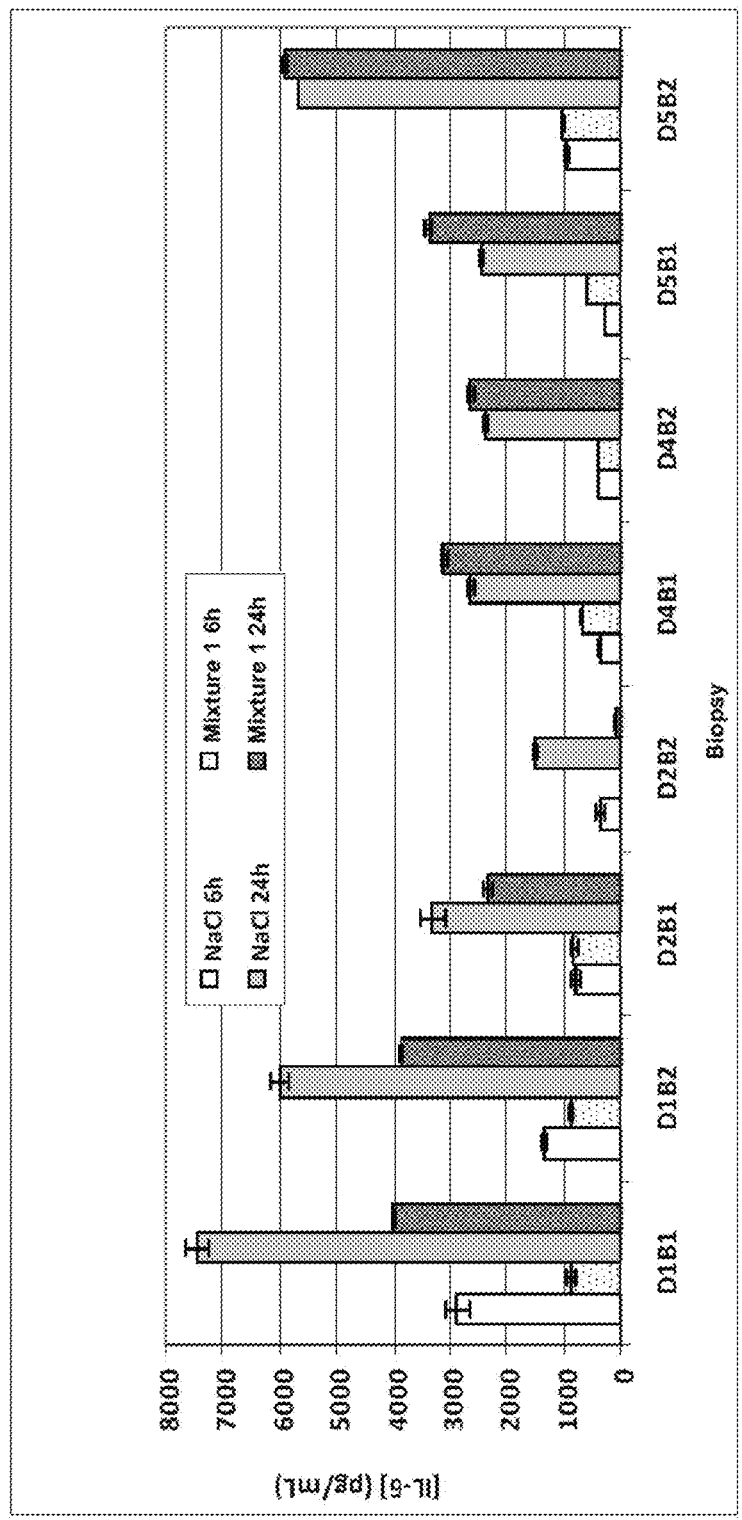
FIG. 6 illustrates the production of interleukin-6 (IL-6) in the culture supernatants of non-pathological human skin biopsies (2 mins) stimulated by the Mixture 1 (24.3 μM of active substance) or NaCl (100 mM) as a control. (D1-5: donor 1 to 5, B1 or 2: biopsy 1 or 2).
Figure 7:
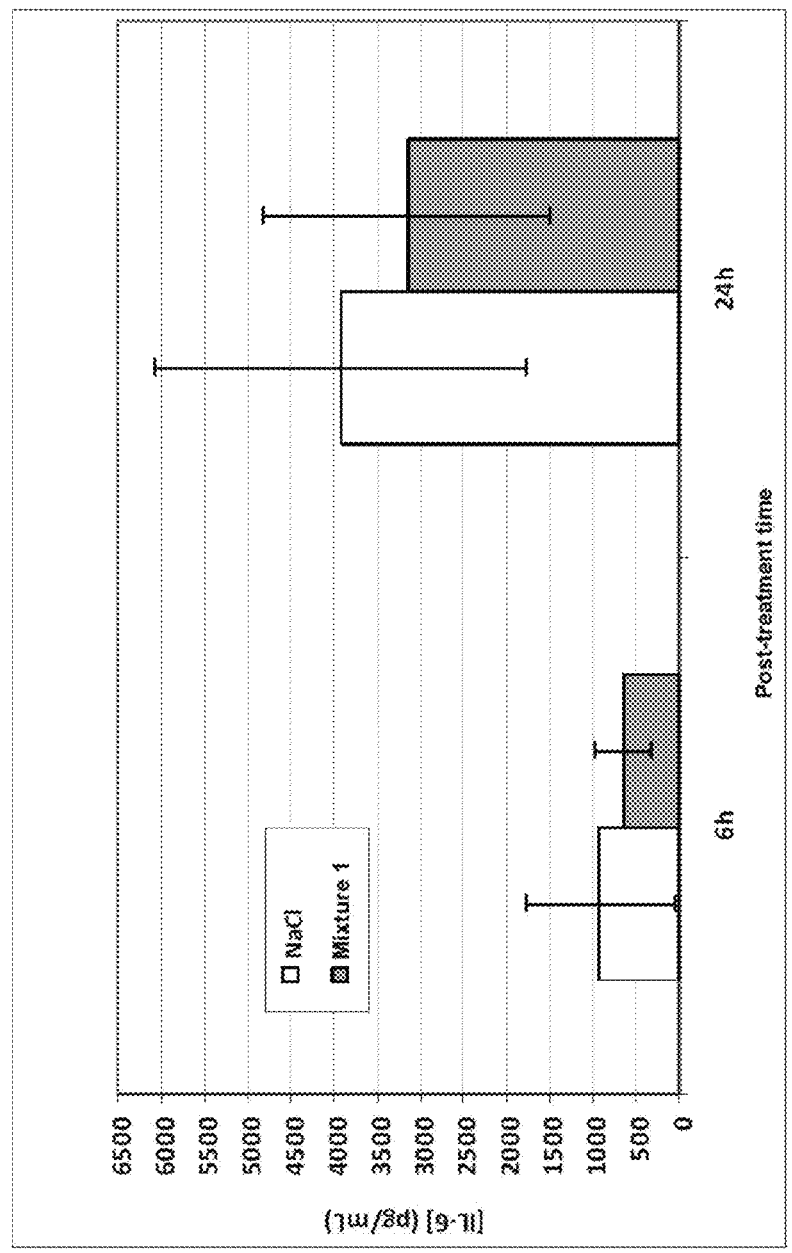
FIG. 7 illustrates the average of the production at 6 h and 24 h after contact with interleukin-6 (IL-6) in the culture supernatants of non-pathological stimulated human skin biopsy (2 mins) by the Mixture 1 (24.3 μM of the active substance) or NaCl (100 mM) as a control.

Conclusions:
production and overproduction heterogeneity (6 h and 24 h, respectively) for IL-6 post-contact NaCl and Mixture 1 (FIG. 6).
a heterogeneous inhibition of production of IL-6 post-contact with Mixture 1 (5 mg/L of active substance) which is on average 28% at 6 h and 19% at 24 h, relatively to the NaCl control (FIG. 6).
By this production inhibition, Mixture 1 has the property of being an anti-inflammatory (FIG. 7).

Example 8—Plasma Degradation and ½ Life

One of the donors of radicals (mainly $HO_2*$, which has a lifetime up to a few seconds and a notable cell penetration index) by a reaction of the Fenton-Haber-Weiss type of the active substance $MoO_4^{2-}$ of the Mixture 1 is $H_2O_2$. The degradation of this tracer was followed for evaluating the consumption rate of the Mixture 1 or its deactivation.

Technique:
The Mixture 1 (68.9 µM or final 14.2 µg/L) was incubated in fresh human plasma. The $H_2O_2$ disappearance kinetics were followed by a peroxidase reaction on aliquots sampled at successive times.

Results:
On average (n=10), the percentage of degradation of the tracer substance of the Mixture 1 in human plasma at room temperature after a contact time of 2 mins is of 85.3±9.4%, 74%±15.2% of which in the first minute.
In the first minute, the "Degradation Time 50%" or $DT_{50}$=0.812 mins for a solution of Mixture 1 at an initial 68.9 µM of active substance and initial 1 mM of $H_2O_2$.
The degradation rate $K_{cH2O2}$: ≈740 µmoles of Mixture 1 at an initial 1 mM of $H_2O_2$/min./L of plasma or $K_{cMoO42-}$: ≈51.0 µmoles of Mixture 1 at initial 68.9 µM of active substance $MoO_4^{2-}$/min/L of plasma, in the first minute of incubation at room temperature.
For a sample of 200 µL of the Mixture 1 at 24.3 µM (5.0 mg/L) of active substance or 353 mM (12 g/L) of the $H_2O_2$ tracer, within the scope of a topical therapeutic application, there are ≈5 nmoles of active substance $MoO_4^{2-}$ or 70 µmoles of $H_2O_2$ tracer. This sample, in 1 L of plasma, is degraded within ≈0.1 minute.

Example 9—Limited Hematotoxicity on Peripheral Blood

The goal of this study is to evaluate the hematotoxicity of the Mixture 1 (24.3 µM or final 5.0 mg/L) after incubation of 2, 3 and 5 minutes in human peripheral blood. The toxicity for which the haematolysis is evaluated following the main blood parameters, i.e. the counts of erythrocytes, leukocytes, the hematocrit, of the platelets, the average globule volume and the hemoglobin level.

Conclusions:
The hematological parameters relating to the counts of erythrocytes, leukocytes, the hematocrit, the average globule volume and the hemoglobin level are not modified by an incubation for up to 5 mins with the mixture according to the invention.
The platelet count is modified by the contact with Mixture 1 from −35% immediately after as soon as its addition, at −69% at 5 minutes.

Example 10—Limited Transcutaneous Passage of the Mixture According to the Invention, Absorption, Biophase and Bioavailability (OECD 428; EMEA, Human Guideline, 2001)

The Mixture 1 used was five times more concentrated (Mixture 1×5) so as to show the smallest passages of substances. The goal of this study was to evaluate (reference t0, t2 min., to t60 min) the passage of the Mixture 1×5 as well as that of the tracer $H_2O_2$ through non-pathological human skin biopsies.

This procedure is applied to three types of substrate: total biopsy, dissected biopsy in the epidermis on the one hand and in the dermis on the other hand.

Technique:
12 biopsies from 2 donors were tested (measurements in the drop deposited on the flap [30 µL]) and in the medium below the latter [800 µL]) according to both methods (Table 4): i) quercetin which evaluates the redox efficiency of the Mixture 1×5 and, ii) the peroxidase which measures the tracer $H_2O_2$ concentration.

The drop (30 µL) deposited above the biopsies and the epidermal and dermal flaps is 5 times more concentrated in active substance (121.5 µM or 25.02 mg/L) and in tracer (1.77 M or 60 g/L) than the therapeutic formulation (24.3 µM or 5.0 mg/L and 352.8 mM or 12 g/L, respectively). In the 30 µL of the Mixture 1×5 deposit, there are 3.65 nmoles or 750 ng of active substance and 53 µmoles or 1.8 mg of tracer.

Results:

TABLE 4

|  | Test | Trial | Biopsy* | Epidermis* | Dermis* |
|---|---|---|---|---|---|
| Drop | 1 | Redox efficiency | −1.4 to −10.5 | −5.7 to −23.9 | NT |
|  | 2 | $H_2O_2$ tracer | −16.5 to −57.7 | −72.5 to −99.9 | −99.6 |
| Medium | 3 | Redox efficiency | +3.7 to +9.0 | +0.5 to +80.6 | +44.5 to +100 |
|  | 4 | $H_2O_2$ tracer | <+0.001** to +0.09 | +0.38 to +1.7 | +0.16 to +0.46 |

*in % relatively to t0 (−: decrease, +: increase)
**detection limit.

A low-to-moderate decrease (test 1) of the redox efficiency of the Mixture 1 is observed in the drop above the flap (from −1.4 to −23.9%).
A moderate-to-significant decrease (test 2) of the amount of the tracer $H_2O_2$ of the Mixture 1 is observed in the drop above the flap (from −16.5 to −99.9%).
A slight-to-significant increase (test 3) of the redox efficiency of the medium under the flap is observed. It depends on the flap and on its type. When this is a complete biopsy, this increase due to the transcutaneous passage is low. On average it is of 6.35% and corresponds to the passage of 232 pmoles (47.6 ng) of active substance of the Mixture 1. When this is the epidermis or the dermis, this increase is highly variable (from 0.8 to 100%). This is most likely due to differences in the histological structures (pores, dermal blood irrigation, epidermal nerve terminations, for example).

An increase from non-detectable to slight (test 4) of the amount of the tracer $H_2O_2$ in the medium under the flap is observed regardless of its type (from <+0.001 to 1.7%). When this is a complete biopsy, this increase due to the transcutaneous passage is particularly low (<0.53 to 47.7 nmoles, i.e. <0.018 to 1.62 µg). When this is the epidermis or the dermis, on average, this increase is low (1.04 and 0.31%, i.e. 0.55 µmoles and 0.16 µmoles, or 18.7 µg and 5.6 µg, respectively).

Conclusions:

There is tissue independence (absorption, deactivation, permeation) of the two parameters considered as typical of Mixture 1 which are the redox efficiency due to the active substance and the dosage of the peroxide tracer, a donor of radicals.

By considering total biopsy, the penetration index of the Mixture 1 corresponds to the thickness of the flap, i.e. 1 mm (average thickness of an epidermis) to 2 mm.

The epidermis contains many nerve terminations which may be the center of axone desalting of herpetic virions in the patient. They are the targets of the Mixture 1 in the same way as the infected epidermal cells or before a potential infection. By considering the succession of both tissues, the biophase of the Mixture 1 is quasi strictly the one of the thickness of the epidermis (1 mm) and is attained in totality for maximum target tissue absorption.

By considering that the dermis alone is vascularized, at most 80.6% of the redox efficiency of the Mixture 1 may be again found at its contact and 1.7% of the tracer. Under these experimental conditions, the bioavailability of the Mixture 1×5 is of 2.94 nmoles or 605 ng of the active substance and 0.9 µmoles or 30.6 µg of peroxide tracer.

In a genotoxicity study in vitro, with the Ames test, the mixture according to the invention and its metabolites is not mutagenic in the presence of the activator S9 (5/5 strains of *Salmonella*), it is mutagenic on 1/5 strain in its absence.

In local application on the skin either stimulated or not, the mixture according to the invention (24.3 µM or 5.0 mg/L of active substance) does not have any associated irritation toxicity.

In a buccal and vaginal irritation study, the mixture according to the invention (24.3 µM or 5.0 mg/L) is not irritating (score 0/16) and very weakly (score 1/16), respectively.

In a highly sensitive study of irritation of the chorioallantoic membrane of a hen egg, the Mixture 1 (18.23 and 24.3 µM or 3.75 and 5.0 mg/L) is moderately irritating (Irritation index or IS=6.8±0.4 and 6.3±0/21, respectively).

In an acute toxicity study by dermal application, the mixture according to the invention at the doses of 25.0 and 31.3 µg/kg of active substance contained in 60 and 75 mg/kg of $H_2O_2$ tracer, respectively, is well tolerated without any symptoms, for a "Maximum Tolerated Dose" (MTD) and a "Maximum Dose Without Any Observable Detrimental Effect" (MDWNODE) or "No Observed Adverse Effect Level" (NOAEL) of 31.3 µg/kg of active substance and 75 mg/kg of tracer.

In an acute toxicity study with intravenous injection, the mixture according to the invention at the doses of 10.4 and 12.5 µg/kg of active substance contained in 25 and 30 mg/kg of $H_2O_2$ tracer, respectively, is tolerated without any notable symptoms for a "Maximum Tolerated Dose" (MTD) of 12.5 µg/kg of active substance.

Example 11—Acceptable Toxicity of the Mixture According to the Invention

I—Mutagenicity In Vitro (Ames Test—OECD 471)

The goal of this study was to evaluate the mutagenic activity of the active mixture according to the invention (Mixture 1) and of its metabolites (produced by the S9 fraction of a rat liver) on the strains of *Salmonella typhimurium* TA97a, TA98, TA100, TA102 and TA1535.

Conclusions:

Without any S9 activation system, the active mixture (7.7 µM or 2.43 µM, i.e. 1.58 mg/L or 0.50 mg/L) according to the invention and its metabolites do not have any mutagenic effects on the TA97a, TA98, TA100 and TA1535 lines.

With an activation system S9, the active mixture (Mixture 1×5: 121.5 µM or 25.02 mg/L) according to the invention and its metabolites do not have any mutagenic effects on the TA97a, TA98, TA100, TA102 and TA1535 lines.

Without the activation system S9, the active mixture according to the invention is not mutagenic on the TA102 strain at 0.50 mg/L.

In this test in vitro, the mutagenic effect of the active mixture and of its metabolites according to the invention is limited for its uses (strain TA102).

II—Dermato-Sensitization after Induction (Hamster Female; OECD 406, ISO 10993-10: 2013 and ICH Memorandum SCCP 2005)

According to the protocol of Magnusson & Kligman (Magnusson B. et al (1969) "*The identification of contact allergens by animal assay. The guinea pig maximization test*", J. Invest. Dermatol., 52(3), 268-276), the sensitization potentialities of the skin of hamster females were studies according to three protocols.

Protocol 1: Determination of the tolerated limiting dose

Concentrations of Mixture 1 from 1.25 mg/L to 20.00 mg/L of active substance contained in 3 g/L to 48 g/L of $H_2O_2$ tracer, respectively, in a 1 ml «patch» were applied for 24 h on the flank of the animals, and then the animals were observed.

The concentration of the Mixture 1 at 10 mg/L of active substance contained in 24 g/L of the tracer is well tolerated and causes moderate irritation.

The concentration of the Mixture 1 at 5.0 mg/L of active substance contained in 12 g/L of $H_2O_2$ tracer is well tolerated and is considered as the maximum non-irritating dose.

Protocol 2: Determination of the tolerated limiting dose after induction by subcutaneous injection.

Concentrations from 5 mg/L to 10 mg/L of active substance contained in 12 g/L to 24 g/L of the $H_2O_2$ tracer, respectively, of the Mixture 1 were injected (100 µL) via a subcutaneous route. At 8 days (first challenge), a first topical application as a 1 ml "patch" was achieved. At 27 days (second challenge), a second topical application as a 1 ml «patch» was achieved. The observations were made at 29 days.

The concentration of the Mixture 1 at 5 mg/L of active substance, contained in 12 g/L of the tracer, is well tolerated and does not produce any irritation.

Protocol 3: Study of the irritation induced by stimulation and topical application of the Mixture 1 at 5 mg/L of active substance contained in 12 g/L of the $H_2O_2$ tracer.

100 µl of Mixture 1 at 5.0 mg/L was injected via a subcutaneous route. At 4 days, the injected area was stimulated with a solution of sodium dodecyl sulfate (SDS) at 10% before topical application of the Mixture 1 (1 ml) in a "patch". At 6 days, a second topical application was achieved. At 21 days (challenge) a topical application of the Mixture 1 (1 ml) in a «patch» with concentrations from 6.26 to 10 mg/L of active substance contained in 15 to 24 g/L of tracer was achieved.

The Mixture 1 at 5.0 mg/L of active substance contained in 12 g/L of tracer is well tolerated and the cutaneous sensitization score by the formulation is equal to 0/3.

Conclusions: The Mixture 1 at 5.0 mg/L of active substance is not irritating. No macroscopic alteration of the skin of the animals was observed. Accordingly, there is no need of any anatomo-pathological study.

III—Buccal and Vaginal Irritation (Female Rabbit; OECD (99)20, -21, -23 -24, -(951115, -(02) 9 and ISO-10993-10: 2013)

The goal of this study was to evaluate the vaginal and buccal tolerance of the Mixture 1 at 5.0 mg/L of active substance contained in 12 g/L of tracer according to an exposure compliant with a 5-day human therapeutic use.

From day 0 to day 6, every 24 h, the animals are treated (1 ml) via a buccal and vaginal route. At day 7, the animals are observed and their weight measured.

Conclusions: The concentration of the Mixture 1 at 5.0 mg/L of active substance is well tolerated. The buccal and vaginal irritation index is 0/16 and 1/16, respectively. Accordingly, there is no need for an anatomo-pathological study.

IV—Ocular Irritation Test (ICCVAM App B)

The ocular irritation test used was the substitution test HET-CAM (Hen's Egg Test—Chorioallantoic Membrane), published in the Official Journal dated Dec. 26, 1996. It is recommended by ICCVAM.

Although this particularly sensitive method is not officially validated by the E.U., it is accepted for a use aiming at locating the even slightly irritating substances including those which would be ocular irritants in order to assign them the label R41 (2002).

Briefly, the method consists of applying a test substance of the Mixture 1 at 3.75 and 5.00 mg/L of an active substance in 9 and 12 g/L of tracer, respectively, on the chorioallantoic membrane of a fertilized hen egg. At 0.5, 2 and 5 mins post-contact, the three following criteria are observed and scored: hemorrhage, coagulation and hyperemia.

Results and Conclusions:

The Mixture 1 at 3.75 mg/L or 5.00 mg/L of active substance may be classified as moderately irritating (Irritation index or IS=6.8±0.4 and 6.3±0/21, respectively), i.e. it induces a slight lysis (severity score=1/3) immediately after its introduction or at 30 s post-contact, no hemorrhage or coagulation.

Considering the Q-value (ratio of the indices between that of the positive substances of reference NaOH 0.1M [IS=15±3] and 1% SDS [10±2] vs. Mixture 1), Q vs. NaOH=0.51 to 0.54 and Q vs. SDS=1.10 to 1.18 for the Mixture 1 at 3.75 and 5.00 mg/L of active substance, respectively.

Accordingly, with regard to this test of an extreme sensitivity, which is much more significant than the already highly performing vaginal irritation test in female rabbits, the Mixture 1 is considered as a slightly (3.75 mg/L) to moderately (5.00 mg/L) irritating substance.

V—Study of the Acute Toxicity by Cutaneous Application and Intravenous Injection—Maximum Tolerated Doses (MTD) and Dose without any Observable Toxic Effect (NOAEL) (Rat; OECD 474, ICH M3(R2) and S6(R1))

The goal of this study is to determine the Maximum Tolerated Dose (MTD) of the Mixture 1 by cutaneous application (1 ml) or intra-caudal injection (5 ml/kg). The clinical observations are reported until day 14.

Conclusions of the Cutaneous Application Protocol:

The Mixture 1 has a dose of 50 µg/kg of active substance (1 ml to 10 mg/L) which is well tolerated. A slight erythema of the treated area is observed as well as the occurrence of small crusts which disappear within 2 days. No irritation is observed.

The same proportionally slighter symptoms are observed for an application of the Mixture 1 of 37.5 µg/kg of active substance (1 ml to 7.5 mg/L).

The Mixture 1 at the doses of 25.0 and 31.3 µg/kg of active substance (1 ml at 5.0 and 6.26 mg/L) is well tolerated. No cutaneous, metabolic or physiological symptom is observed at D14.

The MTD of the Mixture 1 in a cutaneous application in rat is of 31.3 µg/kg of active substance (1 ml to 6.26 mg/L).

The NOAEL (dose without any observable toxic effect) of the Mixture 1 in cutaneous application in rats is of 31.3 µg/kg of active substance (1 ml at 6.26 mg/L).

Conclusions of the Intra-Caudal Injection Protocol:

The difficulty of intravenous administration of the Mixture 1 does not lie in an intrinsic toxicity of the invention but on its decomposition in contact with blood which notably generates molecular oxygen which may be responsible for embolism. The ethical limiting dose (3 rats) having demonstrated a reversible respiratory arrest is 14.6 µg/kg of active substance (5 ml/kg of the Mixture 1 at 2.92 mg/L). No sign of toxicity was recorded until D14.

The Mixture 1 is tolerated after intravenous injection at 12.5 µg/kg of active substance (5 ml/kg of the Mixture 1 at 2.5 mg/L). Physiological difficulties (movements and respiratory difficulties) were observed in animals at the moment of the injection. No sign of toxicity was recorded until D14.

The same symptoms proportionally less significant were observed after an intravenous injection at 10.4 µg/kg of active substance (5 ml/kg of the Mixture 1 at 2.1 mg/L). No clinical sign or modification of the weight curve was reported. No sign of toxicity was recorded until D14. The macroscopic observation of the organs at D14 after autopsy did not reveal anything.

The MTD of the Mixture 1 in an intra-caudal injection is 12.5 µg/kg of active substance (5 ml/kg of the Mixture 1 at 2.5 mg/L).

VI—Study of the Genotoxicity In Vivo by Searching for the Generation of Micronuclei after Intravenous Injection of the Mixture 1 (Rat Males and Females; OECD 474 and ICH S2(R1))

Rat females (n=5) and male rats (n=5) were injected (two treatments at an interval of 22-26 hours; 5 ml/kg) with the HPLC water carrier (intravenous route), the cyclophosphamide positive controls at 5 and 10 mg/kg, intravenous route and ethyl methanesulfonate at 100 and 150 mg/kg (intraperitoneal route) and the Mixture 1 at 1.46, 4.17 and 12.5 µg/kg of active substance (intravenous route).

The morbidity, the mortality, the weight of the animals and the clinical parameters (temperature, skin, hair, eyes, mucous membranes, secretions and excretions, respiratory and neurological function, gait and posture) were noted. 36 h to 48 h after the second treatment, the blood of the animals was collected and analyzed in flow cytometry (toxicity control: reduction of the proportion of immature erythrocytes (CD-71-positive). The proportion of micro-nucleated immature erythrocytes (reticulocytes) was evaluated on 4,000 observations per blood sample. Each rat population (n=10) for each tested substance represents 40,000 observations (Table 5).

TABLE 5

| Substance | mg/kg | gender | n | Reticulocytes (%) | Micro-nucleated reticulocytes (%) |
|---|---|---|---|---|---|
| Before treatment | # | male | 5 | 4.39 ± 0.92 | 0.15 ± 0.09 |
| | | female | 5 | 2.60 ± 0.57 | 0.17 ± 0.07 |
| Negative control | # | male | 5 | 5.17 ± 1.47 | 0.32 ± 0.31 |

TABLE 5-continued

| Substance | mg/kg | gender | n | Reticulocytes (%) | Micro-nucleated reticulocytes (%) |
|---|---|---|---|---|---|
| Water | | female | 5 | 3.82 ± 0.29 | 0.12 ± 0.04 |
| Positive control 1 | 5 | male | 5 | 3.99 ± 0.49 | 0.56 ± 0.17 |
| Cyclophosphamide | | female | 5 | 2.41 ± 0.54 | 0.40 ± 0.13 |
| | 10 | male | 5 | 1.95 ± 0.59 | 1.62 ± 0.29 |
| | | female | 5 | 1.30 ± 0.43 | 1.02 ± 0.26** |
| Positive control 2 | 100 | male | 5 | 1.41 ± 0.32 | 0.68 ± 0.35** |
| Methanesulfonate | | female | 5 | 1.86 ± 0.25 | 0.48 ± 0.16** |
| | 150 | male | 5 | 1.33 ± 0.34 | 0.81 ± 0.48** |
| | | female | 5 | 0.45 ± 0.33 | 0.59 ± 0.26** |
| Mixture 1 | 1.46 · $10^{-3\#}$ | male | 5 | 5.32 ± 0.76 | 0.10 ± 0.02 |
| | | female | 5 | 3.35 ± 0.46 | 0.09 ± 0.03 |
| | 4.17 · $10^{-3\#}$ | male | 5 | 4.82 ± 0.41 | 0.11 ± 0.03 |
| | | female | 5 | 3.35 ± 0.83 | 0.09 ± 0.02 |
| | 12.5 · $10^{-3\#}$ | male | 5-3* | 4.79 ± 0.16 | 0.22 ± 0.12 |
| | | female | 5-1* | 3.40 ± 0.19 | 0.09 ± 0.02 |

*dead animals during the first treatment by embolism due to the release of molecular oxygen from the Mixture 1 in contact with blood.
**statistically different from the Control group.
in active substance $MoO_4^{2-}$ Conclusion: As compared with the control groups (positive and negative), the Mixture 1 does not have any genotoxicity by inducing production of micro-nucleated reticulocytes after intravenous injection in rats (n=10, including 5 males and 5 females) with a range of 1.46, 4.17 and 12.5 μg/kg of active substance.

Example 12—Comparison with Other Compositions

The present example notably shows the influence of the composition, in particular of the redox potential on:
1—the role of calcium in the Fenton/Haber-Weiss "like" catalysis of the tested formulations.
2—the existence of a difference between three 5.0 mg/L formulations of active substance.

S1: Mixture 1,
S2: composition according to U.S. Pat. No. 6,660,289,
S3: composition according to WO/2010/004161.

Protocol 1 (Tables 6 and 7):

2 measured parameters: i) pH, ii) redox potential.

catalyst $CaCl_2$ (1M, in $H_2O$): addition in a final concentration of 24 mM kinetics: initial (T0), 1, 2, 3 minutes (T1, T2, T3) after adding $CaCl_2$ with stirring.

Results and Discussion:

TABLE 6

| | T0 | $CaCl_2$ 24 mM | T1 | T2 | T3 | Average (between T1 and T3) | Δ/T0 |
|---|---|---|---|---|---|---|---|
| Solution S1 | | | | | | | |
| pH | 4.70 | ↓ at T0 | 4.58 | 4.59 | 4.59 | 4.59 over 3 min. | −0.11 |
| Redox pot. E° (mV) | 359 | | 383 | 383 | 383 | 383 over 3 min. | +24 |
| Solution S2 | | | | | | | |
| pH | 2.85 | ↓ at T0 | 2.65 | 265 | 2.66 | 2.65 over 3 min | −0.20 |
| Redox pot. E° (mV) | 437 | | 479 | 475 | 474 | 476 over 3 min | +39 |
| Solution S3 | | | | | | | |
| pH | 3.01 | ↓ at T0 | 2.86 | 2.87 | 2.87 | 2.87 over 3 min. | −0.14 |
| Redox pot. E° (mV) | 414 | | 465 | 464 | 464 | 464 over 3 min | +50 |

The pH of the skin is from 4.93+/−0.45 to 5.12+/−0.56. The vaginal pH is normally of the order of 4.50 and may range up to 6.00 at the menopause.

the solution S1 is buffered and at a pH of the order of the one of the human skin and mucous membranes. This pH remains relatively constant up to 3 mins of contact after adding $CaCl_2$ final 24 mM. A moderate increase of E° is observed which may partly come from the addition of the chlorine of $CaCl_2$.

An acid pH amplifies the cytotoxic lipid peroxidation mediated by iron.

The solution S2 is not buffered. Its pH is not very compatible for contact with the skin or the mucosas (including the probable destruction of the commensal flora in a therapeutic use). This pH remains relatively constant up to 3 mins of contact after adding $CaCl_2$ at a final 24 mM. An increase at least less moderate vs. S1 of E° is observed which may partly come from the addition of the chlorine of $CaCl_2$.

The solution S3 is not buffered. Its pH is not very compatible for contact with the skin or the mucous membranes (including the probable destruction of the commensal flora in a therapeutic use). This pH remains relatively constant up to 3 mins of contact after adding $CaCl_2$ final 24 mM. A significant increase (+50 mV) of E° is observed which may partly come from the addition of the chlorine of $CaCl_2$ but with regard to the difference in potential increase vs. S1 and S2, there would probably not be this single factor.

As regards the Fe ions in situ, at an acid pH (<2.33), the redox potential is of the order of 400 mV and the Fe in the (III) form, i.e. in its most cytotoxic form. At a pH of the order of 4.5, the redox potential is of the order of 300 mV, the hemoglobin Fe in the (II) form and the plasma Fe complexed with transferrin in the (III) form.

At the pH of the solutions S2 and S3, the iron oxide form $Fe(OH)_3$ is highly disadvantaged. Accordingly, the Fenton-Haber-Weiss reactions are not very effective.

The value of the potential of the pair $Fe(OH)_3/Fe^{2+}$ (Fenton type) is: $E'°=1.19-0.18 \times pH$.

TABLE 7

|  | Act. subst. (mg/L) | pH | $E°_{Fe(OH)3/Fe2+}$ (mV)* | Esolution (mV) |
|---|---|---|---|---|
| S1 | 5.0 | 4.70 | 344 | 354 |
| S2 | 5.0 | 2.80 | 686 | 428 |
| S3 | 5.0 | 3.00 | 650 | 418 |

*in situ cell level with iron

According to this study, there is confirmation that the pair $Fe_{(OH)_3}/Fe^{2+}$ is disadvantaged. Even if the redox potential of this pair is improved (418-428 mV), it remains too significant for cell contact.

the transmembrane potential of an animal cell is negative ($\approx$-70 mV). The more significant is the oxidation-reduction potential of the solution, the more there will be alteration of the transmembrane potential and more there will be induction of the cell oxidative stress (genic induction of apoptosis, of the eNOS routes, . . . ) with concomitantly induction of a calcium influx which potentializes the significant cell stress already induced by the solutions 2 and 3.

Accordingly, the pH and the redox potential of formulation S2 and especially the redox potential of the formulation S3 are most likely cytotoxic. Both of these solutions S2 and S3 cannot be suitable for therapeutic use.

Protocol 2 (Table 8):

The cell and plasma concentrations of calcium are of the order of 2 to 3 mM. This protocol is based on a therapeutic use of the formulations.

1 measured parameter: residual amount of peroxides ($H_2O_2$, peracetic acid; test range Quantofix between 0 and 25 mg/L).

catalyst $CaCl_2$) (1M, in $H_2O$): addition in a final concentration of 1.25, 2.5, 10, 25 and 50 mM.

final volume: 1 ml=0.950 µL of tested solution+0.05 µL of the $CaCl_2$ dilution. The dilution factor of the tested solution: 1.05. Final concentration of the tested solution 11.4 g/L (initial 12 g/L) of the tracer $H_2O_2$ containing 4.76 mg/L of active substance (initial 5.00 mg/L).

kinetics: 5 minutes after adding $CaCl_2$ with stirring.

Results:

TABLE 8

| Test | Tested | Final [$CaCl_2$] (mM) | [peroxides]$_{final}$ (mg/L) |
|---|---|---|---|
| 1 | S1 | 50 | >>25 |
| 2 | S1 | 25 | 10-25 |
| 3 | S1 | 10 | 10 |
| 4 | S1 | 2.5 | 5-10 |
| 5 | S1 | 1.25 | ≈25 |
| 6 | S2 | 2.5 | >25 |
| 7 | S3 | 2.5 | >25 |
| 8 | S3 | 1.25 | ≈25 |

The deactivation of the formulation S1 at 5 minutes of contact with $CaCl_2$ 2.5 mM (physiological concentration) corresponds to a peroxide decrease by a factor 1,500 (Test 4), i.e. from 12 g/L to 8 mg/L of tracer and 5.00 mg/L to 3.33 µg/L of active substance).

Comparatives Conclusions Concerning the Formulations S2 and S3

The solution S2, regardless of the metal used, is not compatible with a therapeutic application, by:
its non-bufferable pH for retaining its potentialities,
its cytotoxic redox potential,
its relative independence to calcium catalysis,
its cytotoxicity under physiological conditions due to $H_2O_2$ and peracetic acid (in addition to the presence of $Ag^+$ ions, for example, having irreversible cytotoxicity),
under the experimental conditions used, there is no Fenton-Haber-Weiss like catalysis therefore there is no reactive radical production for therapeutic use.

The solution S3, regardless of the metal used and the chelating pair described in patent application WO2010/004161, is not compatible with a therapeutic application, by:
its pH which is not compatible with BAPTA,
its cytotoxic redox potential,
its relative independence to calcium catalysis,
its cytotoxicity under physiological conditions due to $H_2O_2$ and peracetic acid,
under the experimental conditions used, there is no Fenton-Haber-Weiss like catalysis, therefore there is no reactive radical production for therapeutic use.

On the contrary, the reaction chemical model of the formulation S1 according to the invention is correct because of its destabilization by calcium.

For the formulation S1, the selections:
of the pH,
of the buffering pair (addition of a single element of the pair: acetic acid, since peracetic acid is slightly produced in situ),
of the transition metal and of its valences compatible with the Fenton-Haber-Weiss like reactions or not,
of the pair of chelating agents (compatibility between them with $Kd_{Ca2+}$ and $Kd_{Mo}$, $Kd_{Fe2+/Fe3+}$ in a "cascade"),
the non cell penetration of chelating agents,
of the activation of the complex of the solution S1 by calcium or other existing metal ions in situ, at physiological doses and pH (importance of the selection of the chelating agents), at a redox potential limiting the lipid oxidations notably (little production of Fe(III)) and the instantaneous generation of permeating reactive radicals at a short range, without accumulation, make this formulation compatible with therapeutic use.

The solution S1 is very strongly degraded at physiological concentrations of calcium with a minimum at 2.5 mM. A reduction (1.25 mM) or an increase (from 10 to 50 mM) of this non-physiological calcium concentration strongly alters this degradation of the peroxides due to the Fenton-Haber-Weiss like reactions by displacement of the equilibria (mass action law). The chemical complex corresponding to the solution S1 is totally adapted to a specific reaction in the cellular and plasma calcium constant.

Example 13—Example of an Active Mixture According to the Invention with a Combination of Mo and La This example of composition ("Mixture 2") according to this invention is made with a molybdenum salt and a lanthanum salt. A composition of the formula according to Table 9 is prepared, expressed as the initial concentration of the components:

TABLE 9

| Substances | Mixture of the invention |
|---|---|
| Sodium Molybdate | 20.7 µM |
| Lanthanum Nitrate | 11.5 µM |
| BAPTA | 42 µM |
| EGTA | 1051.6 µM |
| $H_2O_2$ | 353 mM |
| $CH_3COOH/CH_3COONa$ | 70 mM |
| pH (by NaOH) | 4.4-5.0 |
| $E°_{rédox}$ | 300 to 420 mV |

The composition is called "initial" because it corresponds to the concentrations of the added reagents without taking into account the catalytic process used.

All the substances used in the synthesis and the finished product are validated by IR-FT spectrum.

TABLE 10

| Product | Purity | Molecular Formula | N° CAS |
|---|---|---|---|
| Sodium Molybdate dihydrate | 98-103% | Na2MoO4•2H2O | 10102-40-6 |
| lanthanum Nitrate hexahydrate | ≥99% | La(NO3)3•6H2O | 10277-43-7 |
| BAPTA: (1,2-bis(o-aminophenoxy)ethane-N,N,N',N'-tetraacetic acid) | ≥98% | C22H24N2O10 | 85233-19-8 |
| EGTA: (ethylene glycol-bis(2-aminoethylether)-N,N,N',N'-tetraacetic acid) | ≥99% | C14H24N2O10 | 67-42-5 |
| Hydrogen Peroxyde | 29-31% | H2O2 | 722-84-1 |
| Glacial Acetic acid* | 99.8-100.5% | CH3COOH | 64-19-7 |
| Sodium Acetate trihydrate | 99-101% | C2H3NaO2•3H2O | 5010524 |
| Sodium hydroxyde | 10N | NaOH | 1310-73-2 |
| Demineralized water | 1 µS | H2O | 7732-18-5 |

The active substance is: $(MoO_4)^{1-}$, $Na^+$ (lanthanum hydroperoxomolybdate).

Molecular Weight: 481.81 g/mol.

Manufacturing Process:

The manufacturing process is identical to that of Mixture 1 in Example 1, with the exception of the modifications described below:

Two SC solutions are being prepared:

| | |
|---|---|
| Solution A - $Na_2MoO_4•2H_2O$ (source of Mo(VI); 100%) | 200 mg |
| | (final 2.4 mM) |
| Water | qsp 340 ml |
| Gentle agitation, room temperature | |
| Solution B - $La(NO_3)_3•6H_2O$ (source of La(III); 100%) | 200 mg |
| | (1.4 mM final) |
| Water | qsp 340 ml |
| Gentle agitation, room temperature | |
| Solution A (10 mL) and then solution B (10 mL) are gradually introduced into the Si2 solution to prepare an S1 solution of lanthanum hydroperoxomolybdate | |
| STEP (vii): Adding chelating agents - Preparation of an S4 solution | |
| Introduction BAPTA (98.8%) | 20 mg/L, |
| Introduction EGTA (99.1%) | 400 mg/L |
| The pH of the final solution is adjusted by NaOH to 4.67 | |
| The final $E_{redox}$ is: 380 mV | |

In Mixture 2, the final concentration of $La(MoO_4)^{1-}$, $Na^+$ is: 20.8 µM.

Figure 8:
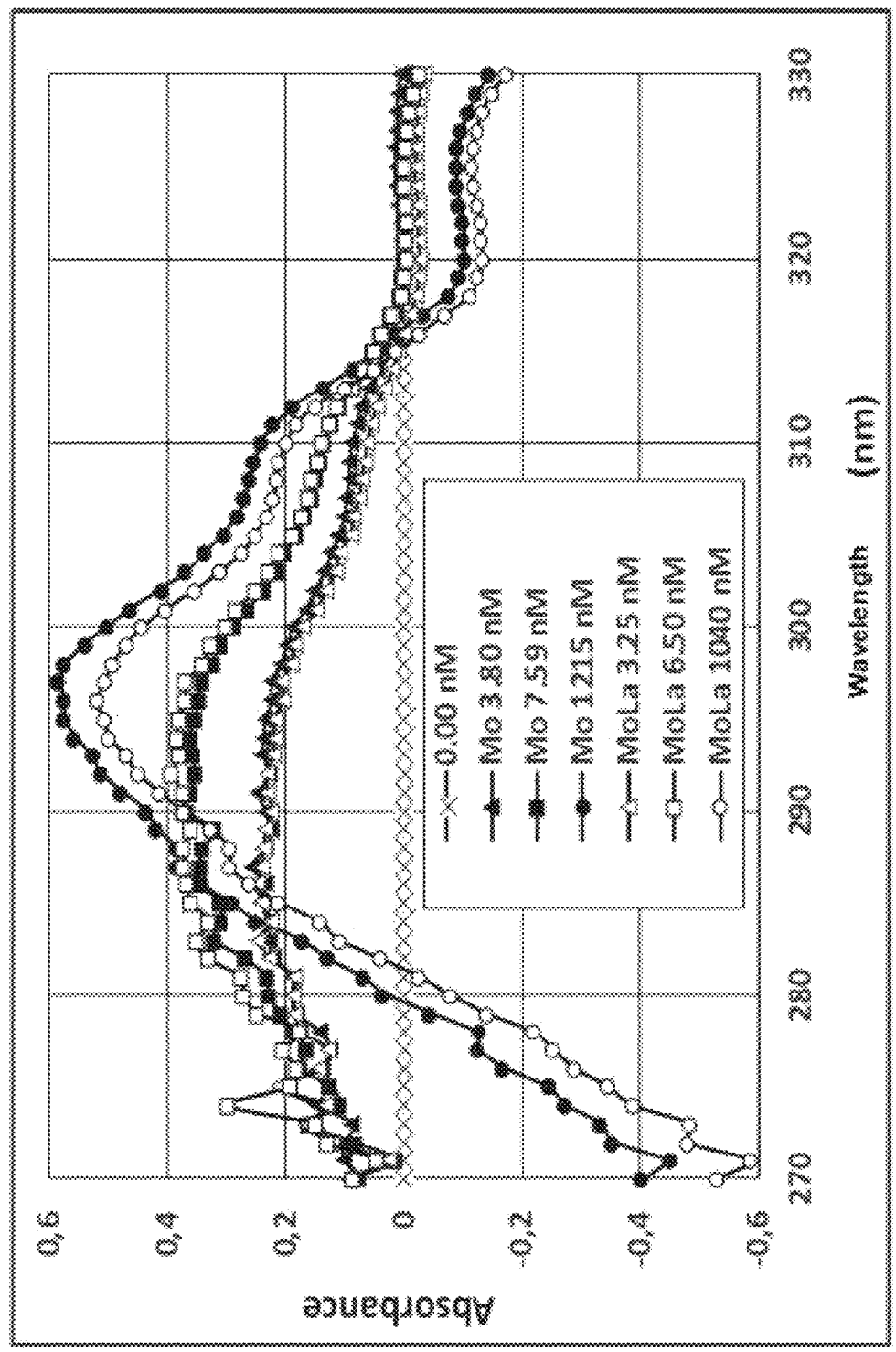
FIG. 8 is a representation of the redox effectiveness of Mixture 1 and Mixture 2 at different concentrations (absorbance of quercetin by Fe(III) in human plasma media after contact (2 min.) with Mixture 1 (in nM $MoO_4^{2-}$) or with Mixture 2 (in nM $La(MoO_4)^{1-}$).

Example 14—Evaluation of the Oxidoreductive Efficiency of the Invention in Double Complex Molybdate and Lanthanate on Human Plasma In order to compare the oxidative efficiency of the $(MoO_4)^{2-}$ (Mixture 1) and $La(MoO_4)^{1-}$ (Mixture 2) formulations, formulations with concentrations comparable to those described in FIG. 3 and lower than those described in FIG. 5 were contacted with human plasma for 2 min. After subtraction of the experimental blanks, specifically in this concentration zone, Mixtures 1 and 2 according to the invention generate an increase in the in situ production of oxidized quercetin. The final concentrations of $MoO_4^{2-}$ and $La(MoO_4)^{1-}$ tested were then: 0.00, 3.80, 7.59, 1215 nM and 0.00, 3.25, 6.50, 1,040 nM, respectively (FIG. 8).

The difference in oxidized quercetin production (apex around 295 nm) between the two formulations (Mixture 1 and Mixture 2) is not significant. The oxidoreductive efficiency between the two compositions according to the invention is comparable.

The invention claimed is:

1. A topical pharmaceutical composition, wherein said composition comprises or consists of a therapeutically active mixture comprising:
    from 0.1 to 100 µM of metal salt of molybdenum;
    at least one chelating agent;
    at least one source of peroxidizing radicals;
    at least one buffering agent,
        wherein said composition or mixture has a redox potential from 250 to 550 millivolts.

2. The topical pharmaceutical composition, according to claim 1, wherein said therapeutically active mixture has a redox potential from 300 to 450 millivolts.

3. The topical pharmaceutical composition, according to claim 1, wherein said therapeutically active mixture comprises from 1 to 50 µM of metal salt of molybdenum.

4. The topical pharmaceutical composition, according to claim 1, wherein said therapeutically active mixture comprises from 5 to 30 µM of metal salt of molybdenum.

5. The topical pharmaceutical composition, according to claim 1, wherein said therapeutically active mixture comprises a peroxo or hydro-peroxomolybdate complex or a mixture thereof.

6. The topical pharmaceutical composition, according to claim 1, wherein said therapeutically active mixture comprises $(Mo_2O_6)^{4+}$ or $[Mo_4O_{12}(O_2)_2]^{4+}$ a mixture thereof.

7. The topical pharmaceutical composition, according to claim 1, wherein the chelating agent is selected from among BAPTA, EGTA and any mixtures thereof.

8. The topical pharmaceutical composition, according to claim 7, wherein said therapeutically active mixture comprises 0.1 to 100 µM of BAPTA.

9. The topical pharmaceutical composition, according to claim 7, wherein said therapeutically active mixture comprises 5 to 20 µM of BAPTA.

10. The topical pharmaceutical composition, according to claim 7, wherein said therapeutically active mixture comprises from 20 to 80 µM of BAPTA.

11. The topical pharmaceutical composition, according to claim 7, wherein said therapeutically active mixture comprises from 0.1 to 1 mM EGTA.

12. The topical pharmaceutical composition, according to claim 7, wherein said therapeutically active mixture comprises from 50 to 800 µM EGTA.

13. The topical pharmaceutical composition, according to claim 7, wherein said therapeutically active mixture comprises from 200 to 2,000 µM EGTA.

14. The topical pharmaceutical composition, according to claim 1, wherein the molybdenum salt and the chelating agents are present according to a ratio from 10/1 to 1/100, expressed in molar concentrations.

15. The topical pharmaceutical composition, according to claim 1, wherein said therapeutically active mixture comprises hydrogen peroxide at a concentration ranging from 200 to 600 mM.

16. The topical pharmaceutical composition, according to claim 1, wherein said therapeutically active mixture comprises from 30 mM to 4.4 M of hydrogen peroxide.

17. The topical pharmaceutical composition, according to claim 1, wherein said composition is buffered at a pH from 4.0 to 5.2.

18. The topical pharmaceutical composition, according to claim 1, wherein said composition comprises:
Molybdate salt;
BAPTA;
EGTA;
$H_2O_2$;
$CH_3COOH/CH_3COONa$;
$E_{redox}$ from 300 to 450 mV; and
pH 4.4-5.0.

19. The topical pharmaceutical composition, according to claim 1, wherein said composition comprises:
Molybdate salt;
Lanthanum salt;
BAPTA;
EGTA;
$H_2O_2$;
CH3COOH/CH3COONa;
Eredox from 300 to 450 mV; and
pH 4.4-5.0.

20. The pharmaceutical composition for topical use according to claim 1, wherein said composition comprises from 0.001 to 5 mM of said pharmaceutically active mixture.

21. A method for a therapeutic treatment of a viral infection, wherein said method comprises administering in a subject in need thereof an effective amount of a topical pharmaceutical composition according to claim 1.

22. The method according to claim 21, wherein the method is performed for therapeutic treatment of an infection involving HSV-1 and/or HSV-2.

23. A method for a therapeutic treatment of a viral infection, wherein said method comprises administering in a subject in need thereof an effective amount of a topical pharmaceutical composition according to claim 18.

24. The method according to claim 23, wherein the method is performed for therapeutic treatment of an infection involving HSV-1 and/or HSV-2.

25. A method for a therapeutic treatment of a viral infection, wherein said method comprises administering in a subject in need thereof an effective amount of a topical pharmaceutical composition according to claim 19.

26. The method according to claim 25, wherein the method is performed for therapeutic treatment of an infection involving HSV-1 and/or HSV-2.

27. A method for preparing a topical composition as defined according to claim 1, wherein said method comprises
(i) the preparation of a buffering solution (BS) comprising a buffering agent having an acid pH,
(ii) the preparation of a solution of a metal complex (SC) comprising a metal oxide salt,
(iii) the preparation of a first initial solution (Si1) comprising hydrogen peroxide,
(iv) the preparation of a second initial solution (Si2) by mixing the BS solution with the Si1 solution,
(v) the preparation of a solution (S1) comprising a peroxo-metal compound by mixing the SC solution with the Si2 solution,
(vi) the preparation of a solution S2 by adjusting the pH of the solution S1 with a base, the pH of the solution S2 being more basic than the pH of the solution BS,
(vii) the addition to the solution S2 of one or several chelating agents,
(viii) the optional adjustment of the pH of the solution resulting from step (vii),
(ix) the optional adjustment of the volume of the solution resulting from step (vii) or step (viii), and
(x) the obtaining of a mixture or of a composition as defined according to claim 1 resulting from step (vii) or optional step (viii) or optional step (ix).

28. The method, according to claim 27, wherein the hydrogen peroxide is present in the Si1 solution at a concentration ranging from 200 to 600 mM.

29. The method, according to claim 27, wherein the buffering agent of the BS solution is a carboxylic acid/carboxylate buffer, and the BS solution has a hydrogen peroxide/carboxylate ratio comprised between 20/1 and 1/1, the ratio being based on molar concentrations.

30. The method, according to claim 27, wherein the method comprises a measurement of the redox potential in steps (iii) to (ix).

31. The method, according to claim 27, wherein the peroxo-metal compound of the solution S1 is a peroxo-molybdenum compound.

* * * * *